(12) United States Patent
Taya et al.

(10) Patent No.: US 12,105,068 B2
(45) Date of Patent: Oct. 1, 2024

(54) INFORMATION PROCESSING DEVICE, INFORMATION PROCESSING DEVICE CONTROL METHOD, PROGRAM, CALCULATION DEVICE, AND CALCULATION METHOD

(71) Applicant: CANON KABUSHIKI KAISHA, Tokyo (JP)

(72) Inventors: Akihiro Taya, Kanagawa (JP); Hidetaka Kawamura, Kanagawa (JP); Yutaka Yoshimasa, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 622 days.

(21) Appl. No.: 17/244,422

(22) Filed: Apr. 29, 2021

(65) Prior Publication Data

US 2021/0248417 A1    Aug. 12, 2021

Related U.S. Application Data

(63) Continuation of application No. PCT/JP2019/044993, filed on Nov. 18, 2019.

(30) Foreign Application Priority Data

Nov. 19, 2018 (JP) .................................. 2018-216857
Dec. 26, 2018 (JP) .................................. 2018-243766

(51) Int. Cl.
*G01N 30/88* (2006.01)
*G01N 30/86* (2006.01)
(Continued)

(52) U.S. Cl.
CPC ............ *G01N 30/86* (2013.01); *G01N 30/88* (2013.01); *G06F 18/214* (2023.01); *G06N 3/045* (2023.01);
(Continued)

(58) Field of Classification Search
CPC ................... G01N 30/86; G01N 30/88; G01N 2030/8804; G01N 2030/8895;
(Continued)

(56) References Cited

U.S. PATENT DOCUMENTS 5,218,529 A * 6/1993 Meyer ...................... G06N 3/02
706/924
2004/0199336 A1   10/2004 Ito
(Continued)

FOREIGN PATENT DOCUMENTS

JP      H06-094696 A      4/1994
JP      H06-505815 A      6/1994
(Continued)

OTHER PUBLICATIONS

PCT International Preliminary Report on Patentability and Written Opinion of the International Searching Authority issued in International Application No. PCT/JP2019/044993 on May 25, 2021.
(Continued)

*Primary Examiner* — Jeffrey P Aiello
(74) *Attorney, Agent, or Firm* — VENABLE LLP

(57) ABSTRACT

Hitherto, preprocessing for separating impurities and calculation processing, for example, a peak splitting method, are required in order to acquire information on test substances from spectral information. An information processing apparatus according to the present invention includes information acquisition means for acquiring quantitative information on a test substance estimated by inputting spectral information on a sample containing the test substance and impurities into a learning model.

17 Claims, 22 Drawing Sheets

(51) Int. Cl.
  *G06F 18/214* (2023.01)
  *G06N 3/04* (2023.01)
  *G06N 3/045* (2023.01)
  *G06N 3/08* (2023.01)

(52) U.S. Cl.
  CPC ....... *G06N 3/08* (2013.01); *G01N 2030/8804* (2013.01); *G01N 2030/8895* (2013.01)

(58) Field of Classification Search
  CPC .............. G06F 18/214; G06F 18/24137; G06F 18/2178; G06F 18/21; G06F 18/25; G06N 3/045; G06N 3/048; G06N 3/08; G06N 3/088; G06N 3/02; G06N 20/00; G16C 20/20; G16C 20/70; G06V 10/82; G06V 10/7715; G06V 10/7784
  USPC ......... 382/128, 133; 435/4; 702/32, 19, 188, 702/22, 2, 183, 189, 104, 27, 1, 23, 85, 702/30; 703/11, 2; 706/12, 16, 15, 1, 706/45, 20
  See application file for complete search history.

(56) References Cited

U.S. PATENT DOCUMENTS

| | | | |
|---|---|---|---|
| 2007/0048746 A1* | 3/2007 | Su | B82Y 15/00 435/7.1 |
| 2010/0153323 A1 | 6/2010 | Hennessy | |
| 2010/0266185 A1* | 10/2010 | Matulewicz | G06T 7/0012 382/131 |
| 2014/0012504 A1* | 1/2014 | Ben-Dor | G01N 33/24 702/2 |
| 2017/0336370 A1 | 11/2017 | Noda | |
| 2018/0268293 A1* | 9/2018 | Noda | G06N 3/043 |
| 2018/0299375 A1* | 10/2018 | Young | G06N 5/01 |
| 2019/0082990 A1* | 3/2019 | Poltorak | A61B 5/7267 |
| 2019/0331562 A1* | 10/2019 | Minobe | G01N 33/493 |
| 2020/0408789 A1* | 12/2020 | Kawamura | G16C 20/20 |

FOREIGN PATENT DOCUMENTS

| | | | | |
|---|---|---|---|---|
| JP | H06-324029 A | | 11/1994 | |
| JP | H07-103959 A | | 4/1995 | |
| JP | 06094696 | * | 4/1996 | ............. G01N 30/86 |
| JP | 2003-161725 A | | 6/2003 | |
| JP | 2006-177980 A | | 7/2006 | |
| JP | 2010-520471 A | | 6/2010 | |
| JP | 2014-134385 A | | 7/2014 | |
| JP | 6280997 B | | 2/2018 | |
| JP | 2018-152000 A | | 9/2018 | |
| WO | 2018/020652 A | | 2/2018 | |
| WO | 2018117129 A1 | | 6/2018 | |
| WO | 2018-134952 A1 | | 7/2018 | |
| WO | 2019092836 A1 | | 5/2019 | |

OTHER PUBLICATIONS

U.S. Appl. No. 17/351,787, filed Jun. 18, 2021 by Hidetaka Kawamura et al.
Kanazawa, Mitsuhiro, Ogiwara, Atsushi, "Automatic peak detection of MS chromatogram using artificial intelligence (AI)", Lecture abstracts of 65th Annual Conference on Mass Spectrometry, Japan, May 1, 2017, p. 102.
"Magnetic Resonance Spectroscopy Quantification Using Deep Learning", by Nima Hatami et al., International Conference on Medical Image Computing and Computer Assisted Intervention, published Sep. 30, 2018, pp. 467-475.
Chinese Office Action issued May 24, 2023 during prosecution of related Chinese Application No. 2019-800761198 (English-language machine translation included.).
European Office Action issued Jul. 24, 2023 during prosecution of related European Application No. 19887559.3.
Brown et al: "Rapid parameter estimation with incomplete chemical calibration models", Chemometrics and Intelligent Laboratory Systems, Elsevier Science Publishers B.V. Amsterdam, NL, vol. 10, No. 1-2, Feb. 1, 1991 (Feb. 1, 1991), pp. 87-105, ISSN: 0169-7439, DOI: 10.1016/0169-7439(91) 80038-R [XP026472504].
Tatiana A. Dolenko, Sergey A. Burikov, Alexander V. Sugonjaev: "Neural network technologies in Raman spectroscopy of water solutions of inorganic salts", Proc. SPIE 5826, OPTO-IRELAND 2005: Optical Sensing and Spectroscopy, Jun. 3, 2005 (Jun. 3, 2005) [XP040205316].
Hatami Nima et al: "Magnetic Resonance Spectroscopy Quantification Using Deep Learning", Sep. 26, 2018 (Sep. 26, 2018), arxiv.org, Cornell University Library, 201 Olin Library Cornell University Ithaca, NY 14853, pp. 467-475 [XP047557637].
Georgouli Konstantia et al: "Data augmentation in food science: Synthesising spectroscopic data of vegetable oils for performance enhancement", Journal of Chemometrics., vol. 32, No. 6, Jun. 1, 2018 (Jun. 1, 2018), p. e3004, GB ISSN: 0886-9383, DOI: 10.1002/cem.3004 Retrieved from the Internet: URL:https://bureadmin.qub.ac.uk/ws/portalfiles/portal/139857071/DataAugmentationPaper_revised.pdf> [XP055854020].
Esben Jannik Bjerrum et al: "Data Augmentation of Spectral Data for Convolutional Neural Network (CNN) Based Deep Chemometrics", arxiv.org, Cornell University Library, 201 Olin Library Cornell University Ithaca, NY 14853, Oct. 5, 2017 (Oct. 5, 2017), [XP080826305].
European Search Report issued Jul. 11, 2022 in corresponding EP Application No. EP19887559.
Japanese Search Report issued Nov. 14, 2023 in corresponding Japanese Application No. 2019-208332 (English-language machine translation included).
Japanese Search Report issued Mar. 26, 2024 in corresponding Japanese Patent Application No. 2019-208332 (English translation available).
Japanese Office Action issued Aug. 15, 2024 in corresponding Japanese Patent Application No. 2019-208332 (machine generated English translation included).

* cited by examiner

INFORMATION PROCESSING DEVICE, INFORMATION PROCESSING DEVICE CONTROL METHOD, PROGRAM, CALCULATION DEVICE, AND CALCULATION METHOD

CROSS-REFERENCE TO RELATED APPLICATIONS

This application is a Continuation of International Patent Application No. PCT/JP2019/044993, filed Nov. 18, 2019, which claims the benefit of Japanese Patent Application No. 2018-216857, filed Nov. 19, 2018, and Japanese Patent Application No. 2018-243766, filed Dec. 26, 2018, all of which are hereby incorporated by reference herein in their entirety.

BACKGROUND OF THE INVENTION

Field of the Invention

The present invention relates to an information processing apparatus, a control method for an information processing apparatus, a program, a calculation apparatus, and a calculation method.

Description of the Related Art

A spectrum analysis is widely used as a method for recognizing a concentration and a quantity of a specific component (hereinafter referred to as "test substance") contained in various samples. In the spectrum analysis, a response exhibited when a certain stimulus is applied to a sample is detected, and information (spectral information) on components forming the sample can be acquired based on the acquired signal. The spectral information is an intensity of an electromagnetic wave including light, as well as the temperature, the mass, and the count of fragments each having a specific mass, which characterize the stimulus and the response. The spectrum analysis also includes using electron collision as the stimulus and recording the quantity of the mass of fragments generated by decomposition, to thereby acquire information, for example, structure.

The spectrum analysis also includes a method in which difference in 3D size, electric charge, and hydrophilic/hydrophobic property among components is used to try separation in advance and then an electromagnetic wave is irradiated, to thereby execute analysis. This method is called "separation analysis." For example, in high performance liquid chromatography (hereinafter referred to as "HPLC"), analysis conditions such as a column type, a mobile phase, a temperature, and a flow rate are optimized, to thereby separate test substances and other materials (hereinafter referred to as "impurities"). After that, the spectrum of each separated test substance is measured, thereby being capable of recognizing the concentration and the quantity. Moreover, when the separation from the impurities is difficult, preprocessing for removing a part of the impurities may be executed, or optimization of separation conditions may be considered. When the impurities cannot be separated through the preprocessing and the optimization of the separation conditions, peak splitting is tried through calculation processing.

In Japanese Patent Application Laid-Open No. H06-324029 and Japanese Patent Application Laid-Open No. 2006-177980, there is a related-art peak splitting method, there exist a method of providing a baseline (FIG. 5), a method of vertically splitting the spectrum through use of a minimal value between peaks (FIG. 6), and a method of fitting an appropriate function, for example, a Gaussian function, through the minimum square method, to thereby split the spectrum.

The HPLC is often used to analyze a sample derived from a living body. However, a sample derived from a living body, such as urine and blood, contains a large quantity of impurities, and may contain unknown impurities derived from intake materials. Accordingly, there is required an operator skilled in consideration of splitting conditions and preprocessing for separating the test substances from the impurities, the peak splitting method, and the like.

Moreover, there is also often a case in which a large quantity of impurities are contained in a sample in analysis of pesticide residue in food, environment analysis impurities, and the like. Thus, there has been a strong demand for a method enabling even a beginner to simply and accurately analyze test substances in a sample containing impurities without requiring preprocessing.

As described above, hitherto, the preprocessing for separating impurities and the calculation processing, for example, the peak splitting method, are required in order to acquire the information on the test substances from the spectral information.

SUMMARY OF THE INVENTION

In order to solve the above-mentioned problem, according to one aspect of the present invention, there is provided an information processing apparatus including information acquisition means for acquiring quantitative information on a test substance estimated by inputting spectral information on a sample containing the test substance and impurities into a learning model, wherein the learning model is generated based on spectral information for learning generated based on spectral information on the test substance.

Further, according to another aspect of the present invention, there is provided a control method for an information processing apparatus, the control method including an information acquisition step of acquiring quantitative information on a test substance estimated by inputting spectral information on a sample containing the test substance and impurities into a learning model, wherein the learning model is generated based on spectral information for learning generated based on spectral information on the test substance.

In order to solve the above-mentioned problem, according to another aspect of the present invention, there is provided a calculation apparatus including: a reception unit configured to receive spectral information on a sample containing a test substance; an acquisition unit configured to acquire a learning model relating to spectral information on the test substance; and a calculation unit configured to calculate quantitative information on the test substance based on the spectral information on the sample and the learning model.

Further, according to another aspect of the present invention, there is provided a calculation method including: a reception step of receiving spectral information on a sample containing a test substance; an acquisition step of acquiring a learning model relating to spectral information on the test substance; and a calculation step of calculating quantitative information on the test substance based on the spectral information on the sample and the learning model.

Further features of the present invention will become apparent from the following description of exemplary embodiments with reference to the attached drawings.

DESCRIPTION OF THE EMBODIMENTS

First Embodiment

Figure 1:
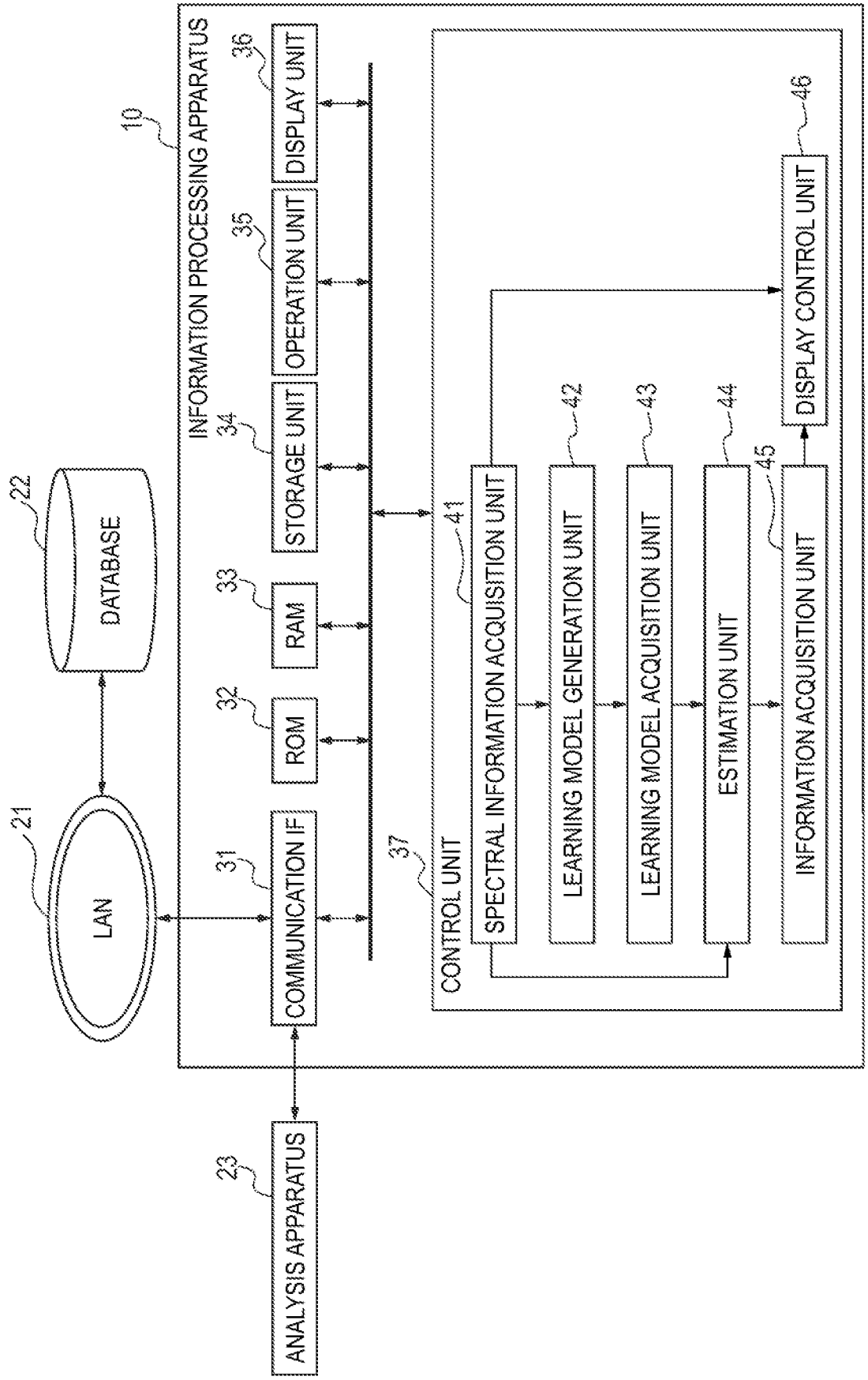
FIG. 1 is a schematic block diagram of an information processing apparatus according to a first embodiment of the present invention.

Embodiments of the present invention are described with reference to drawings. The scope of the present invention is not limited to each of the embodiments described below.

First, terms are described before the description of this embodiment.

(Sample)

A sample in this embodiment is a mixture configured to contain a plurality of kinds of compounds. In this embodiment, the sample is not particularly limited as long as the sample is a mixture containing a test substance and any other substance (impurity). In addition, it is not required that components of the mixture be specified, and an unknown component may be contained. For example, the sample may be a mixture derived from a living body, such as blood, urine, or saliva, or may be food and beverage. The analysis of a sample derived from a living body provides clues to understand the nutrition and health conditions of a sample donor, and is hence medically and nutritionally valuable. For example, urinary vitamin B3 is involved in the metabolism of carbohydrates, lipids, and proteins, and energy production, and hence the measurement of N1-methyl-2-pyridone-5-carboxamide, which is a urinary metabolite of the vitamin B3, is useful for nutritional guidance for maintaining good health.

(Test Substance)

A test substance in this embodiment includes one or more known components contained in the sample. For example, the test substance is at least one kind selected from the group consisting of proteins, DNA, viruses, fungi, water-soluble vitamins, fat-soluble vitamins, organic acids, fatty acids, amino acids, saccharides, pesticides, and endocrine disrupters.

For example, when the quantities of nutrients are to be clarified, water-soluble vitamins, such as thiamine (vitamin B1), riboflavin (vitamin B2), N1-methylnicotinamide and N1-methyl-2-pyridone-5-carboxamide, which are each a metabolite of vitamin B3, 4-pyridoxic acid, which is a metabolite of vitamin B6, N1-methyl-4-pyridone-3-carboxamide, pantothenic acid (vitamin B5), pyridoxine (vitamin B6), biotin (vitamin B7), pteroylmonoglutamic acid (vitamin B9), cyanocobalamine (vitamin B12), and ascorbic acid (vitamin C), amino acids, such as L-tryptophane, lysine, methionine, phenylalanine, threonine, valine, leucine, isoleucine, and L-histidine, and minerals, such as sodium, potassium, calcium, magnesium, and phosphorus, may be used as the test substances.

(Quantitative Information)

In this embodiment, for example, the quantity of the test substance contained in the sample, the concentration of the test substance contained in the sample, or the presence or absence of the test substance in the sample may be used as quantitative information. In addition, for example, the ratio of the concentration or quantity of the test substance in the sample with respect to the reference quantity of the test substance, or the ratio between the quantities of the test substances contained in the sample or between the concentrations of the test substances may be used as other quantitative information on the test substance.

(Spectral Information)

Spectral information in this embodiment is at least one kind selected from the group consisting of a chromatogram, a photoelectron spectrum, an infrared absorption spectrum (IR spectrum), a nuclear magnetic resonance spectrum (NMR spectrum), a fluorescence spectrum, a fluorescent X-ray spectrum, an ultraviolet/visible absorption spectrum (UV/Vis spectrum), a Raman spectrum, an atomic absorption spectrum, a flame emission spectrum, an optical emission spectrum, an X-ray absorption spectrum, an X-ray diffraction spectrum, a paramagnetic resonance absorption spectrum, an electron spin resonance spectrum, a mass spectrum, and a thermal analysis spectrum.

(Information Processing System and Information Processing Apparatus)

With reference to FIG. 1, an information processing system in this embodiment is now described. FIG. 1 is a diagram for illustrating an overall configuration of the information processing system including an information processing apparatus according to this embodiment.

The information processing system includes an information processing apparatus 10, a database 22, and an analysis apparatus 23. The information processing apparatus 10 and the database 22 are connected to each other for communication through communication means. In this embodiment, the communication means is formed of a local area network (LAN) 21. Moreover, the information processing apparatus 10 and the analysis apparatus 23 are connected to each other through communication means compliant with a standard, for example, the universal serial bus (USB). The LAN may be a wired LAN or a wireless LAN, or may be a wide area network (WAN). Moreover, the USB may be a LAN.

The database 22 manages spectral information acquired through analysis by the analysis apparatus 23. Moreover, the database 22 manages learning models (learned models) generated by a learning model generation unit 42 described below. The information processing apparatus 10 acquires the spectral information and the learning models managed by the database 22 through the LAN 21.

(Learning Model)

The learning model in this embodiment is a regression learning model, and a regression learning model generated through machine learning, for example, deep learning, may be used. A learning model that is built so that learning is executed by applying training data to a machine learning algorithm for appropriate estimation is herein referred to as "learning model." There are various types of machine learning algorithms to be used for the learning model. For example, deep learning using a neural network can be used. The neural network is formed of an input layer, an output layer, and a plurality of hidden layers. The layers are connected to each other through calculation expressions referred to as "activation functions." When labeled (output corresponding to input) training data is used, coefficients of the activation functions are determined so that a relationship between the input and the output is satisfied. A learning model capable of highly accurately predicting output corresponding to input can be generated by determining the coefficients through use of a plurality of pieces of training data.

(Analysis Apparatus)

The analysis apparatus 23 is an apparatus configured to analyze a sample, a test substance, and the like. The analysis apparatus 23 corresponds to an example of analysis means. In this embodiment, as described above, the information processing apparatus 10 and the analysis apparatus 23 are communicably connected to each other. However, the information processing apparatus 10 may internally include the analysis apparatus 23, or the analysis apparatus 23 may internally include the information processing apparatus 10. Further, analysis results (spectral information) may be passed from the analysis apparatus 23 to the information processing apparatus 10 through a recording medium, for example, a nonvolatile memory.

The analysis apparatus 23 in this embodiment is not limited as long as the analysis apparatus can acquire the spectral information, and an apparatus configured to use a chemical analysis method or to use a physical analysis method may be used. In this embodiment, the apparatus configured to use a chemical analysis method is configured to use at least one kind of method selected from the group consisting of chromatography, such as liquid chromatography and gas chromatography, and capillary electrophoresis. In this embodiment, the apparatus configured to use a physical analysis method is configured to use at least one kind of method selected from the group consisting of photoelectron spectroscopy, infrared absorption spectroscopy, nuclear magnetic resonance spectroscopy, fluorescence spectroscopy, fluorescent X-ray spectroscopy, visible/ultraviolet absorption spectroscopy, Raman spectroscopy, atomic absorption spectroscopy, flame emission spectroscopy, optical emission spectroscopy, X-ray absorption spectroscopy, X-ray diffractometry, electron spin resonance spectroscopy using paramagnetic resonance absorption or the like, mass spectroscopy, and thermal analysis.

For example, an apparatus configured to use liquid chromatography includes a mobile phase container, a liquid feed pump, a sample injection unit, a column, a detector, and an A/D converter. As the detector, for example, an electromagnetic wave detector using, for example, ultraviolet light, visible light, or infrared light, an electrochemical detector, or an ion detector is used. In this case, the resultant spectral information is information on an output intensity from the detector with respect to time.

The information processing apparatus 10 includes, as its functional components, a communication interface (IF) 31, a ROM 32, a RAM 33, a storage unit 34, an operation unit 35, a display unit 36, and a control unit 37.

The communication interface (IF) 31 is implemented by, for example, a LAN card and an interface card for USB. The communication IF 31 manages communication between external apparatus (such as the database 22 and the analysis apparatus 23) and the information processing apparatus 10 through the LAN 21 and the USB. The read only memory (ROM) 32 is implemented by a nonvolatile memory or the like, and stores various types of programs and the like. The random access memory (RAM) 33 is implemented by a volatile memory or the like, and temporarily stores various types of information. The storage unit 34 is implemented by, for example, a hard disk drive (HDD) or the like, and stores various types of information. The operation unit 35 is implemented by, for example, a keyboard, a mouse, and the like, and inputs instructions from a user into the apparatus. The display unit 36 is implemented by, for example, a display or the like, and displays various types of information to the user. The operation unit 35 and the display unit 36 provide functions as a graphical user interface (GUI) through control from the control unit 37.

(Control Unit)

The control unit 37 is implemented by, for example, at least one central processing unit (CPU) or the like, and integrates and controls processing performed in the information processing apparatus 10. The control unit 37 includes, as its functional components, a spectral information acquisition unit 41, the learning model generation unit 42, a learning model acquisition unit 43, an estimation unit 44, an information acquisition unit 45, and a display control unit 46.

(Spectral Information Acquisition Unit)

The spectral information acquisition unit 41 acquires analysis results of a sample containing at least test substances and impurities, specifically, spectrum information on the sample, from the analysis apparatus 23. The spectral information acquisition unit 41 acquires the spectral information on the sample from the database 22 that stores the analysis results in advance. Moreover, the spectral information acquisition unit 41 similarly acquires spectral information on the test substance. The spectral information on the test substance is spectral information at the time when the test substance alone exists. After that, the spectral information acquisition unit 41 outputs the acquired spectral information on the sample to the estimation unit 44. Moreover, the spectral information acquisition unit 41 outputs the acquired spectral information on the test substance to the learning model generation unit 42. There is now described a case in which a plurality of types of the test substances are contained in the sample, but the number of the types of the test substances may be one.

(Splitting Unit)

The spectral information acquisition unit 41 in this embodiment may further include a splitting unit (not shown) configured to split the spectral information on the sample. The splitting unit can split the spectrum information on the sample containing test substances and impurities into spectrum information on each test substance.

An example of a method of splitting spectral information on the sample into a plurality of pieces of spectral information is a method of specifying, by the user, splitting locations of the spectral information. For example, there exist a method of specifying a range of a spectrum for each test substance, and a method of specifying a center of the spectrum for each test substance, to thereby extract a certain range before and after the center. The method of specifying the center includes a method of setting the range to be extracted in advance and a method of automatically determining the range to be extracted in accordance with a position (a retention time in a case in which the spectral information is a chromatogram) in the spectral information. For example, when the chromatogram is acquired through, for example, liquid chromatography, as the retention time becomes longer, the chromatogram is more likely to be broad, and it is thus only required to extend a range for the extraction. That is, it is only required to change the range to be extracted from the chromatogram in accordance with the retention time of the chromatogram. For example, when the test substance having a peak appearing at a position corresponding to a long retention time in a chromatogram is treated, it is only required to extend the range to be extracted from the chromatogram.

Another example of the method of splitting spectral information on the sample into a plurality of pieces of spectral information is a method of automatically determining the splitting locations of the spectral information. For example, a threshold value is provided for the spectral information, and when the threshold value is exceeded, it can be determined that spectral information on the test substance exists at the position of the excess. For example, for spectral information having a Gaussian distribution, a center point between two points at which the threshold value is exceeded is a peak center of the spectral information. The peak height is obtained from the peak center, and a standard deviation ($\sigma$) can be acquired from the full width at half maximum. In this method, it is preferred to set the range to be extracted from the peak center based on "$\sigma$". It is preferred that the range to be extracted be from about $\pm 2\sigma$ to about $\pm 4\sigma$.

Regarding the range for extracting the spectral information, an optimal range is highly likely to change in accordance with the type of test substance. Thus, after the extraction range is determined, a learning model may be created by the generation unit described below. Then, the accuracy may be checked, and after that, the extraction range may be corrected. Specifically, after the extraction range is determined, the spectral information is extracted in the range, and the learning model is created by the generation unit descried below. A sum (B) obtained by adding noise to extracted spectral information (A) is input to the created learning model, and a correlation coefficient between output C and the spectral information A (such as the peak height and the peak area) is obtained. The extraction range is changed, and the correlation coefficient is checked by the same method. Then, it is possible to determine whether the extraction range is to be increased or reduced in accordance with a change in the correlation coefficient.

Further, when the spectral information is to be split, machine learning may be used. The spectral information can be split into the spectral information on each test substance by learning splitting locations for various types of spectral information.

(Learning Model Generation Unit)

The learning model generation unit 42 generates training data through use of the spectral information on the test substance acquired by the spectral information acquisition unit 41. After that, the learning model generation unit 42 executes the deep learning through use of the training data, to thereby generate the learning models. The generation of the training data and the generation of the learning models are described in detail below. After that, the learning model generation unit 42 outputs the generated learning models to the learning model acquisition unit 43. The learning model generation unit 42 may output the generated learning models to the database 22.

An example of the generation method for the learning models is now described. First, the location of the information on each test substance is extracted from the analysis results containing the test substances. The method for the extraction is the same as the means for the splitting in the splitting unit described above. As a result, when the spectral information has been split in advance in the splitting unit, the location of the information is not required to be extracted again. When the spectral information has not been split, the spectrum for each test substance is extracted from the spectral information by the same method as that of the splitting unit. Data containing increased and reduced quantities of the information on each test substance is generated based on the extracted information (peak position) on each test substance. For example, when there are peaks of three test substances A, B, and C, there are generated peak shapes that are 0 times, 0.2 times, 0.4 times, 0.6 times, 0.8 times, 1.2 times, 1.4 times, 1.6 times, and 1.8 times of the original peak height of the test substance A. Similarly, the peak shapes are generated also for the test substances B and C. In this example, 10 types of peak shapes of each test substance are generated. It is preferred that the peak shapes to be generated correspond to an expected range including the test substance. Moreover, as the number of peak shapes to be generated increases, the accuracy of the learning model increases.

There exist roughly two methods for generating the learning model.

One method is to use training data obtained by combining generated peaks of the respective test substances. In the above-mentioned example, there exist the three components, which are the test substances A, B, and C, and the number of total combinations is thus 10×10×10=1,000. Data for input is generated by adding any waveforms generated based on random numbers to the combination. As data for output, the peak height of each test substance used for the data for input is prepared, and a combination of the input data and the output data is used as training data. In this case, one learning model is to be generated.

Another method is to generate a learning model for the generated peak of each test substance. The height of the peak prepared for each test substance is used as the output. As the data for input, a sum obtained by adding any waveform generated from random numbers to the peak shape prepared for each test substance is prepared. The prepared input data and output data are used as the training data. In this case, one learning model is to be generated for each test substance, and thus, in the above-mentioned example, three learning models are to be generated.

In any one of the methods, the any waveform to be generated in accordance with the random numbers is based on information acquired in each analysis method. For example, the spectral information acquired through the liquid chromatography often presents a Gaussian distribution. In such a case, it is preferred that training data include input obtained by adding a plurality of Gaussian curves each having the peak height, a median value, and the standard deviation determined from the random numbers to one another and further adding the analysis results of the test substance and output formed of the analysis results of the test substance. The output may be formed of only information desired to be obtained, for example, the peak height. More specifically, it is preferred that the number of Gaussian curves to be added be a number at which the Gaussian curves cannot be separated from one another on the chromatogram and the peaks of the Gaussian curves are thus likely to overlap. A sufficient number is usually about two to eight for one test substance. When the number exceeds eight, the estimation of the shape of the peak of the test substance becomes more difficult, and the quantification accuracy decreases. When the number is three or less, accurate quantification cannot be achieved for a chromatogram insufficient in separation. The number is preferably three to six, more preferably four or five. The shape of the any waveform is a Gaussian function given by Expression 1.

$$a \exp\left\{-\frac{(x-b)^2}{2c^2}\right\} \quad \text{(Expression 1)}$$

In this expression, "a" is a value at x % from 0 with respect to an expected peak height of the test substance. The value "b" is a value up to x % of a trimmed range (for example, when a range of 3σ from the peak center of the test substance is trimmed, "b" is any value in a range of from −8σ×x % to +8σ×x %), and is determined in accordance with a random number. The value "x" is from 100 to 300, preferably from 100 to 250, more preferably from 100 to 200. The value "c" is preferably determined from a random number in a range of a value from 0.1 times to 10 times, preferably from 0.2 times to 8 times, more preferably from 0.5 times to 5 times, of the standard deviation from the peak of the test substance. The plurality of any waveforms are added to one another for each test substance, and after that, one combination of the training data is obtained by forming a set of the added waveforms and the value to be obtained (for example, the peak heights of the plurality of test substances). About 1,000 to 2,000 combinations of training data are prepared. Similar training data is created for peaks for combinations of the same test substances having different contents. It is preferred that about 5,000 to 20,000 pieces of training data formed of about five to ten types of test substances having different contents be prepared.

Further, the any waveform generated from the random numbers may be prepared in accordance with the position of the spectral information to which the waveform is to be added. For example, in the liquid chromatography, as the retention time of a peak becomes longer, the peak is more likely to be broad. A learning model having a higher accuracy can be generated by setting the standard deviation of the any waveform generated from the random numbers as a function of time and increasing the standard deviation as the retention time becomes longer.

(Learning Model Acquisition Unit)

The learning model acquisition unit 43 acquires the learning models generated by the learning model generation unit 42. When the learning models are stored in the database 22, the learning model acquisition unit 43 acquires the learning models from the database 22. After that, the learning model acquisition unit 43 outputs the acquired learning models to the estimation unit 44.

(Estimation Unit)

The estimation unit 44 inputs the spectral information on the sample acquired by the spectral information acquisition unit 41 to the learning models acquired by the learning model acquisition unit 43, to thereby cause the learning models to estimate quantitative information on the test substances contained in the sample. After that, the estimation unit 44 outputs the estimated quantitative information to the information acquisition unit 45. The estimation unit 44 corresponds to an example of estimation means for estimating the quantitative information on the test substances by inputting the spectral information on the sample to the learning model.

The information acquisition unit 45 acquires the quantitative information estimated by the learning model. That is, the information acquisition unit 45 corresponds to an example of information acquisition means for acquiring the quantitative information on the test substances estimated by inputting the spectral information on the sample containing the test substances and impurities to the learning model. After that, the information acquisition unit 45 outputs the acquired quantitative information to the display control unit 46.

(Display Control Unit)

The display control unit 46 causes the display unit 36 to display the quantitative information acquired by the information acquisition unit 45. The display control unit 46 corresponds to an example of display control means.

At least a part of the components of the control unit 37 may be implemented as an independent apparatus. Moreover, the respective components may be implemented as software achieving the functions. In this case, the software for achieving the function may operate on a server through a network, for example, a cloud. In this embodiment, it is assumed that the components are achieved by the software in a local environment.

The configuration of the information processing system of FIG. 1 is merely an example. For example, the storage unit 34 of the information processing apparatus 10 may have the function of the database 22, and the storage unit 34 may hold the various types of information.

Figure 2:
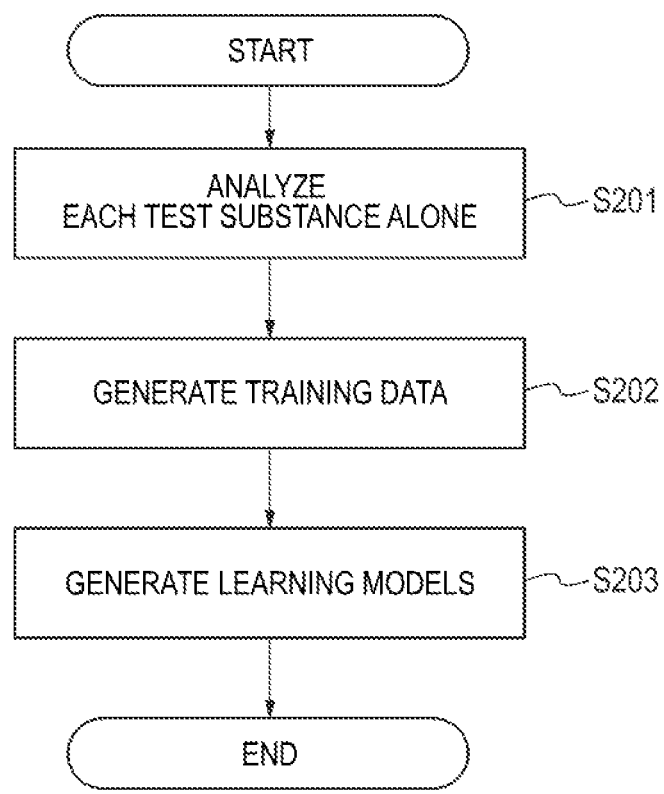
FIG. 2 is an example of a flowchart of a processing procedure relating to generation of learning models in the first embodiment of the present invention.
Figure 3:
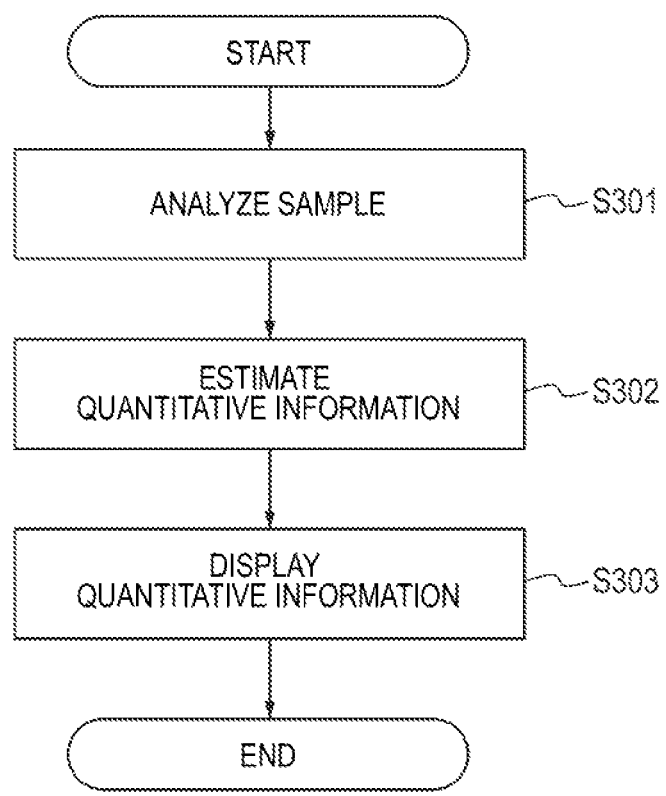
FIG. 3 is an example of a flowchart of a processing procedure for acquiring quantitative information on test substances in the first embodiment of the present invention.

With reference to FIG. 2, a processing procedure in this embodiment is now described. FIG. 2 is a flowchart of the processing procedure relating to the generation of the learning models.

(S201) (Analyze Each Test Substance Alone)

In Step S201, the analysis apparatus 23 analyzes each test substance alone, to thereby acquire the spectral information on the test substances. It is only required to appropriately select analysis conditions in terms of sensitivity, a period of time required for the analysis, and the like. In this analysis, the analysis apparatus 23 executes the analysis at several different concentrations of each test substance. The required number of concentrations depends on a property of the substance and the like, and it is desired that the number be generally three or more. The analysis of the test substances may be executed for each test substance or may be simultaneously executed for the test substances. After that, the analysis apparatus 23 outputs the acquired spectral information to the information processing apparatus 10. The information processing apparatus 10 receives the spectral information from the analysis apparatus 23, and holds the spectral information in the RAM 33 or the storage unit 34. The spectral information acquisition unit 41 acquires the spectral information held as described above. As described above, the database 22 may hold the spectral information being the analysis results. In this case, the spectral information acquisition unit 41 acquires the spectral information from the database 22. Moreover, timing at which the analysis apparatus 23 analyzes the test substances may be any timing as long as the analysis is executed before the generation of the training data in Step S202.

(S202) (Generate Training Data)

In Step S202, the learning model generation unit 42 generates a plurality of pieces of training data through use of the spectral information on the test substances acquired by the spectral information acquisition unit 41. The generation method for the training data is now specifically described. The training data is generated by adding the any waveforms generated from the random numbers to the spectrum information on the test substances. For example, the waveform represented by the spectral information (chromatogram) often presents a Gaussian distribution in the liquid chromatography. As a result, the learning model generation unit 42 adds a plurality of Gaussian curves (Gaussian functions) each having the peak height, the median value, and the standard deviation determined from the random numbers to one another, to thereby generate a plurality of pieces of random noise. After that, the learning model generation unit 42 generates a plurality of waveforms each formed by adding the plurality of pieces of random noise and the spectral information on the test substance to each other. The plurality of waveforms generated as described above are used as spectral information (spectral information for the learning) on a virtual sample containing the test substances and impurities. That is, the generated plurality of pieces of spectral information are determined as the input data forming the training data. Further, the learning model generation unit 42 determines the height (quantitative information) of the peak identified from the spectral information on the test substance being a base of the generated spectral information as correct-answer data forming the training data. As described above, the learning model generation unit 42 generates the plurality of pieces of training data being combinations of the input data and the correct-answer data.

After that, in Step S201, the learning model generation unit 42 has acquired the spectral information corresponding to the concentrations of the test substances, and thus generates a plurality of pieces of training data for each concentration. In consideration of the point that the width of the peak tends to increase as the retention time increases in the waveform of the chromatogram, the learning model generation unit 42 may increase the width of the waveform to be generated.

In Japanese Patent Application Laid-Open No. 2018-152000, there is disclosed a method for machine learning of mass spectral data on a sample in association with presence or absence of cancer. However, in order to increase the accuracy of the machine learning, a large quantity of training data is required. In Japanese Patent Application Laid-Open No. 2018-152000, as the training data, 90,000 types of data are prepared. That is, the machine learning can accurately analyze complicated analysis results, but has a problem in that it is required to prepare a large quantity of training data. In this embodiment, it is not required to prepare a large quantity of training data, which is the problem of the machine learning, and a load on the user can thus be reduced.

The training data is generated as described above, but a plurality of samples may be analyzed by the analysis apparatus 23, to thereby acquire spectral information for learning on the samples, and the training data may be acquired by combining the acquired spectral information with the quantitative information on the test substances. Moreover, the spectral information on the virtual samples may be generated in a method different from the above-mentioned methods.

(S203) (Generate Learning Models)

In Step S203, the learning model generation unit 42 uses the plurality of pieces of training data generated for the respective concentrations in Step S202 to execute the machine learning in accordance with a predetermined algorithm, to thereby generate the learning models. In this embodiment, as the predetermined algorithm, a neural network is used. The learning model generation unit 42 uses the plurality of pieces of training data to cause the neural network to learn, to thereby generate a learning model configured to estimate the quantitative information on each test substance contained in the sample based on the input of spectral information on the sample. A learning method for the neural network is a well-known technology, and a detail description thereof is thus omitted in this embodiment. Moreover, as the predetermined algorithm, for example, a support vector machine (SVM) or a deep neural network (DNN) may be used. As another algorithm, a convolutional neural network (CNN) or the like may be used. When a plurality of types of test substances exist, the learning model is built for each substance. The learning model generation unit 42 stores the generated learning models in the RAM 33, the storage unit 34, or the database 22.

As described above, there is generated the learning model configured to estimate the quantitative information on each test substance contained in the sample based on the spectral information on the sample.

(S301) (Analyze Sample)

In Step S301, the analysis apparatus 23 analyzes a target sample, to thereby acquire the spectral information on the sample. The analysis conditions are the same as those in Step S201. After that, the analysis apparatus 23 outputs the acquired spectral information to the information processing apparatus 10. The information processing apparatus 10 receives the spectral information from the analysis apparatus 23, and holds the spectral information in the RAM 33 or the storage unit 34. The spectral information acquisition unit 41 acquires the spectral information held as described above. As described above, the database 22 may hold the spectral information being the analysis results. In this case, the spectral information acquisition unit 41 acquires the spectral information from the database 22. Moreover, timing at which the analysis apparatus 23 analyzes the sample may be any timing as long as the analysis is executed before the estimation of the quantitative information in Step S302.

(S302) (Estimate Quantitative Information)

In Step S302, the learning model acquisition unit 43 acquires the learning model stored in the RAM 33, the storage unit 34, or the database 22. After that, the estimation unit 44 inputs the spectral information on the sample acquired in Step S301 to the acquired learning models, to thereby cause the learning models to estimate the quantitative information on the test substances contained in the sample. Moreover, the estimation unit 44 converts the estimated quantitative information to a form to be displayed on the display unit 36 in accordance with necessity. The form displayed on the display unit 36 may be concentration such as g/L and mol/L or a ratio to a reference quantity (standard quantity). When the value estimated by the learning model is in the display form, the conversion is not required. After that, the information acquisition unit 45 acquires the estimated quantitative information from the estimation unit 44, and stores the quantitative information in the RAM 33 or the storage unit 34.

As described above, even when the peak of the test substance and the peak of the impurities are not completely separated from each other, it is possible to accurately acquire the quantitative information on the test substance through use of the learning model acquired through the machine learning without complicated and high-level knowledge on the analysis.

As a result, even a person without experience can simply and highly accurately execute the quantitative analysis of the test substances.

(S303) (Display Quantitative Information)

In Step S303, the display control unit 46 causes the display unit 36 to display the quantitative information on the test substances contained in the sample, the quantitative information being estimated by the learning model in Step S302. In this display, the quantitative information may be arranged and displayed in a graph form or a table form.

(Data Analysis Method)

Figure 4:
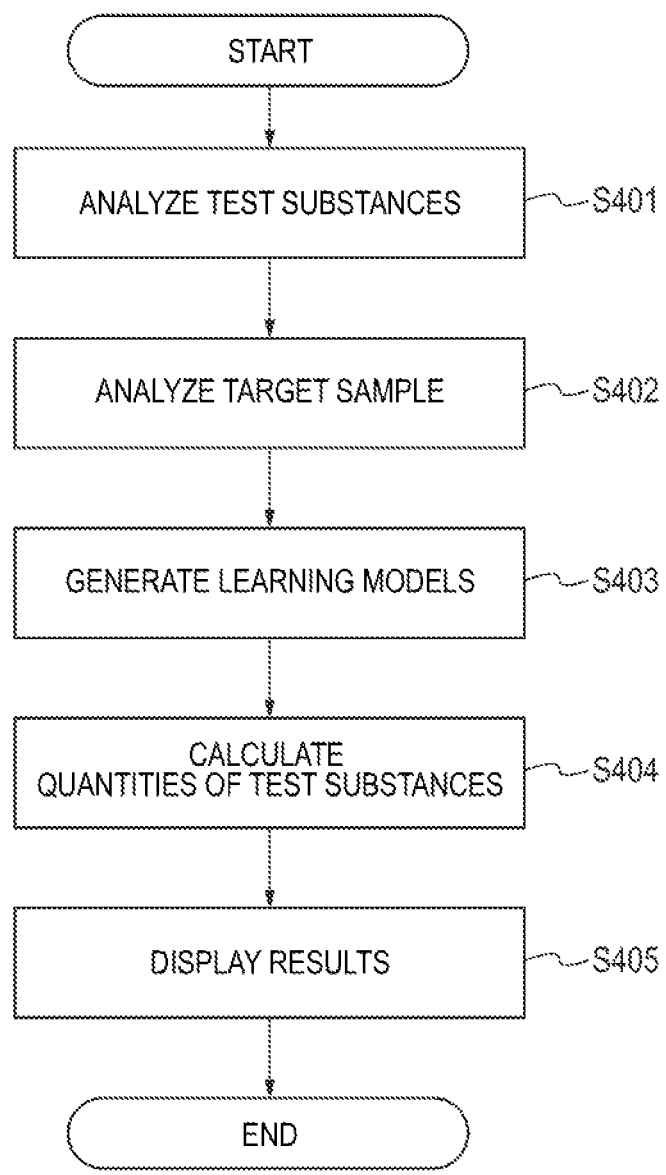
FIG. 4 is an example of a flowchart of processing for calculating quantities of the test substances in a sample in the first embodiment of the present invention.

With reference to FIG. 4, processing performed in a calculation apparatus is now described in more detail. FIG. 4 is a flowchart of processing of calculating the quantities of the test substances in the sample.

First, the analysis unit analyzes the test substances (Step S401). It is only required to appropriately select analysis conditions in terms of sensitivity, a period of time required for the measurement, and the like. In the analysis, the measurement may be made at several different concentrations of each test substance.

Subsequently, the analysis unit analyzes the target sample containing the test substances (Step S402). Measurement conditions are set to the same conditions as those in Step S401.

Subsequently, the generation unit uses the measurement results of the test substances acquired in Step S401 to generate training data. The generation unit uses the generated training data to execute machine learning in accordance with a predetermined algorithm, to thereby build learning models (Step S403). As a specific method for the learning, for example, the neural network, the support vector machine, or the like may be used as a general machine learning method. Moreover, as a deep learning method having a plurality of hidden layers, the deep neural network (DNN), the convolutional neural network (CNN), or the like may be used.

Subsequently, the calculation unit applies each learning model generated in Step S403 to the measurement data acquired in Step S402, to thereby calculate the quantity of each test substance (Step S404). In this calculation, the quantity is converted to the form for the display on the display unit. The form displayed on the display unit may be the concentration such as g/L and mol/L or the ratio to the standard quantity.

Subsequently, the display unit displays the quantities of the test substances calculated in Step S404, to thereby present the quantities to the user (S405). In this display, the quantities may be arranged and displayed in a graph form or a table form.

The present invention can also be implemented by processing of supplying a program for implementing one or more functions of the above-mentioned embodiment to a system or an apparatus through a network or a recording medium and reading out and executing the program by one or more processors included in a computer of the system or the apparatus. Moreover, the present invention can also be implemented by a circuit (for example, an ASIC) configured to implement the one or more functions.

The present invention is described in more detail by way of Examples and Comparative Examples, but the present invention is not limited to the following Examples.

Second Embodiment

Figure 7:
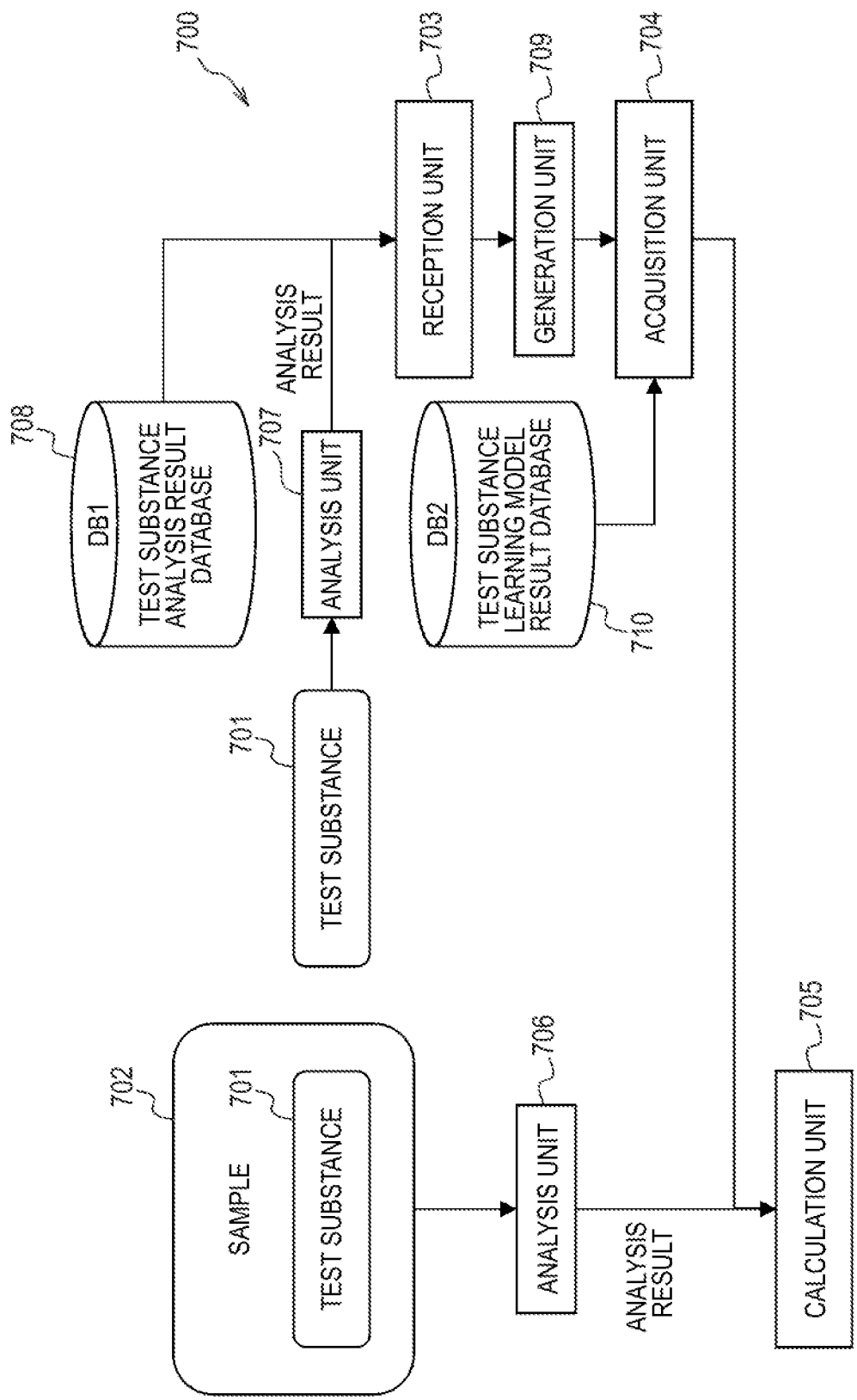
FIG. 7 is a schematic block diagram of a calculation apparatus according to a second embodiment of the present invention.

FIG. 7 is a schematic block diagram of a calculation apparatus according to a second embodiment of the present invention.

(Configuration of Calculation Apparatus)

A calculation apparatus 700 according to this embodiment includes a reception unit 703 and an acquisition unit 704. The reception unit 703 receives analysis results of each test substance 701 alone for a sample 702 containing the test substance 701. The acquisition unit 704 acquires a learning model relating to the analysis results of the test substance. Further, the calculation apparatus 700 includes a calculation unit 705 configured to calculate quantitative information on each test substance through use of the analysis results of the sample and the learning model.

In recent years, there has also been developing an analysis method for complicated analysis results through use of machine learning. In Japanese Patent Application Laid-Open No. 2018-152000, there is disclosed the method for machine learning of the mass spectral data on the sample associated with the presence or absence of cancer. However, in order to increase the accuracy of the machine learning, a large quantity of training data is required. In Japanese Patent Application Laid-Open No. 2018-152000, as the training data, 90,000 types of data are prepared. That is, the machine learning can accurately analyze complicated analysis results, but has the problem in that it is required to prepare a large quantity of training data.

According to this embodiment, even when the peak of the test substance and the peak of the impurities are not completely separated from each other, it is possible to accurately acquire peak information on the test substance through use of the learning model acquired through the machine learning without the complicated and high-level knowledge on the analysis. Moreover, it is not also required to prepare a large quantity of training data, which is the problem of the machine learning.

Moreover, when the peak of the test substance and the peak of the impurities cannot be completely separated from each other, there has hitherto been required an operation requiring the complicated and high-level knowledge relating to the analysis, such as preprocessing and optimization of analysis conditions. According to the calculation apparatus of this embodiment, it is possible to acquire information on the test substances from spectrum information without the preprocessing for separating the impurities and the calculation processing, for example, the peak splitting method.

As a result, even a person without experience can simply and highly accurately execute the quantitative analysis of the test substances.

The calculation apparatus according to this embodiment may further include an analysis unit 706 configured to analyze a sample. Even when the calculation apparatus does not include the analysis unit, the calculation apparatus may acquire analysis results from an analysis unit 707 provided separately or may acquire the analysis results from a database (DB1) 708. Moreover, the learning models may be generated by the generation unit 709 or may be acquired from a database (DB2) 710.

The calculation apparatus according to this embodiment is now described in detail.

(Reception Unit)

The reception unit receives analysis results of a sample, specifically, information on the spectral information on the sample. In order to acquire the analysis results, when the calculation apparatus according to this embodiment includes the analysis unit described below, the calculation apparatus can acquire the spectral information on the sample from the analysis unit. Moreover, when the calculation apparatus according to this embodiment does not include the analysis unit, the database (DB1 of FIG. 7) storing the analysis results may be provided in advance, and the calculation apparatus may acquire the analysis results, that is, the spectral information on the sample, from the database. The database may exist in a storage apparatus built into the calculation apparatus, in a storage apparatus externally mounted to the calculation apparatus, and on a cloud through a network.

(Acquisition Unit)

The acquisition unit acquires the learning models based on the analysis results of the sample acquired by the reception unit. The learning models may be generated by the generation unit described below. Moreover, the database (DB2 of FIG. 7) storing the learning models for the test substances may be provided in advance, and the learning models may be acquired from the database. The database may exist in the storage apparatus built into the calculation apparatus, in the storage apparatus externally mounted to the calculation apparatus, and on the cloud through the network.

(Learning Model)

In this embodiment, a learning model generated through machine learning, for example, deep learning, can be used as the learning model.

A learning model that is built so that learning is executed by applying training data to a machine learning algorithm so as to be able to execute appropriate prediction is herein referred to as "learning model." There are various types of machine learning algorithms to be used for the learning model. For example, deep learning using a neural network can be used. The neural network is formed of the input layer, the output layer, and the plurality of hidden layers. The layers are connected to each other through calculation expressions referred to as "activation functions." When labeled (output corresponding to input) training data is used, coefficients of the activation functions are determined so that a relationship between the input and the output is satisfied. A learning model capable of highly accurately predicting output corresponding to input can be created by determining the coefficients through use of a plurality of pieces of training data.

As the learning model in this embodiment, it is possible to use, for example, information containing spectral information and random noise. The spectral information is spectral information in a case in which the test substance alone exists (spectral information on the test substance). The random noise is not particularly limited, and a waveform being a combination of a plurality of Gaussian functions may be used. Moreover, in consideration of the point that, in the waveform of the chromatogram, he width of the peak tends to increase as the retention time increases, the width of the waveform to be generated may be increased.

(Spectral Information)

In this embodiment, the spectral information is at least one kind selected from the group consisting of a chromatogram, a photoelectron spectrum, an infrared absorption spectrum, a nuclear magnetic resonance spectrum, a fluorescent X-ray spectrum, an ultraviolet/visible absorption spectrum, and a Raman spectrum. In addition, the spectral information is at least one kind selected from the group consisting of an atomic absorption spectrum, a flame emission spectrum, an optical emission spectrum, an X-ray absorption spectrum, an X-ray diffraction spectrum, a paramagnetic resonance absorption spectrum, a mass spectrum, and a thermal analysis spectrum.

(Calculation Unit)

The calculation unit applies the learning model acquired by the acquisition unit to the analysis results of the sample, to thereby calculate quantitative information on the test substances in the sample.

(Analysis Unit)

The analysis unit in this embodiment corresponds to various types of analysis machines each configured to acquire the analysis results of the sample and the test substances. The analysis unit may be provided in a form in which the analysis unit is provided in the same computer as that of at least one other unit of the calculation apparatus as well as a form in which the analysis unit is connected through wired and wireless Internet networks and further, a form in which the analysis results are passed and received through a recording medium, for example, a nonvolatile memory.

The analysis unit in this embodiment is configured to use at least one kind of method selected from the group consisting of chromatography, capillary electrophoresis, photoelectron spectroscopy, infrared absorption spectroscopy, nuclear magnetic resonance spectroscopy, fluorescent X-ray spectroscopy, visible/ultraviolet absorption spectroscopy, and Raman spectroscopy. In addition, the analysis unit is configured to use at least one kind of method selected from the group consisting of atomic absorption spectroscopy, flame emission spectroscopy, optical emission spectroscopy, X-ray absorption spectroscopy, X-ray diffractometry, paramagnetic resonance absorption spectroscopy, mass spectroscopy, and thermal analysis.

Various apparatus are used for the analysis, and examples thereof include an ultraviolet/visible absorption spectrum (UV/Vis spectrum), an infrared absorption spectrum (IR spectrum), a nuclear magnetic resonance spectrum (NMR spectrum), and Raman spectral analysis. Other examples thereof include fluorescence spectral analysis, atomic absorption analysis, an atomic absorption spectrum, flame analysis, a flame fluorescence spectrum, optical emission spectroscopic analysis, an optical emission spectrum, emission X-ray analysis, X-ray diffraction, and fluorescence X-ray diffraction. Further examples thereof include a fluorescent X-ray spectrum, a paramagnetic resonance absorption spectrum, mass spectral analysis, thermal analysis, gas chromatography, liquid chromatography, and a photoelectron spectrum.

For example, for liquid chromatography, a mobile phase container, a liquid feed pump, a sample injection unit, a column, a detector, and an A/D converter are provided. As the detector, an electromagnetic wave detector that uses, for example, ultraviolet ray, visible ray, or infrared ray, an electrochemical detector, an ion detector, or the like is used. In this case, the spectral information to be acquired is an output intensity from the detector with respect to time.

(Generation Unit)

The generation unit generates the learning models by creating training data based on the analysis results of the test substances and executing the deep learning. The training data is generated by adding any waveforms generated from random numbers to the analysis results of the test substance. For example, the spectral information acquired through the liquid chromatography often presents a Gaussian distribution. In such a case, it is preferred that training data include input obtained by adding a plurality of Gaussian curves each having the peak height, the median value, and the standard deviation determined from the random numbers to one another and further adding the analysis results of the test substance and output formed of the analysis results of the test substance. The output may be formed of only information desired to be obtained, for example, the peak height. More specifically, there is prepared data obtained by trimming the analysis results of the test substance while the peak is considered as the center. As the range of the trimming becomes wider, accuracy of the quantification by the subsequent calculation unit increases, but the number of pieces of training data required to increase the accuracy increases. The range to be trimmed is about 6 times to 30 times of the standard deviation (a) from the peak of the test substance. The range is preferably 10 times to 20 times, more preferably 14 times to 18 times, of the standard deviation (a) from the peak of the test substance. After that, the any waveforms are added to the trimmed data. It is preferred that the number of waveforms to be added be a number at which the waveforms cannot be separated from one another on the chromatogram and the peaks of the waveforms are thus likely to overlap, and a sufficient number is usually about two to eight. When the number exceeds eight, prediction of the shape of the peak of the test substance becomes more difficult, and the quantification accuracy thus decreases. Further, when the number is three or less, accurate quantification may not be provided for a chromatogram insufficient in separation. The number is preferably three to six, more preferably four and five. The shape of the any waveform is a Gaussian function given by Expression 1.

$$a \exp\left\{-\frac{(x-b)^2}{2c^2}\right\}$$ (Expression 1)

In this expression, "a" is a value at x % from 0 with respect to an expected peak height of the test substance. The value "b" is a value up to x % of the trimmed range, and is determined in accordance with a random number. For example, when a range of ±3σ from the peak center of the test substance is trimmed, "b" can be any value in a range of from −8σ×x % to +8σ×x %. The value "x" is from 100 to 300, preferably 100 to 250, more preferably 100 to 200. The value "c" is preferably determined from a random number in a range of a value from 0.1 times to 10 times, preferably from 0.2 times to 8 times, more preferably from 0.5 times to 5 times, of the standard deviation from the peak of the test substance. A plurality of any waveforms are added to one another, and after that, one combination of training data can be obtained by forming a set of the added waveforms and the value to be obtained (for example, the peak height of the test substance). About 1,000 to 2,000 pieces of training data are prepared for the peak of one test substance. Similar training data is created for peaks of the same test substances having different contents. It is preferred that about 5,000 to 20,000 pieces of training data formed of about five to ten types of test substances having different contents be prepared.

(Storage Unit)

The calculation apparatus according to this embodiment may further include a storage unit storing the learning models. In this configuration, the acquisition unit can acquire the learning models from the storage unit.

(Display Control Unit)

The calculation apparatus according to this embodiment may further include a display control unit configured to control display of quantitative information.

(Sample)

The sample is not particularly limited as long as the sample is a mixture configured to contain a plurality of kinds of compounds. In addition, it is not required that components of the mixture be specified, and an unknown component may be contained. For example, the sample may be a mixture derived from a living body, such as blood, urine, or saliva, or may be food and beverage. The analysis of a sample derived from a living body provides clues to understand the nutrition and health conditions of a sample donor, and is hence medically and nutritionally valuable. For example, urinary vitamin B3 is involved in the metabolism of carbohydrates, lipids, and proteins, and energy production, and hence the measurement of N1-methyl-2-pyridone-5-carboxamide, which is a urinary metabolite of vitamin B3, is useful for nutritional guidance for maintaining good health.

(Test Substance)

The test substance in this embodiment includes one or more known components contained in the sample. For example, the test substance is at least one kind selected from the group consisting of proteins, DNA, viruses, fungi, water-soluble vitamins, fat-soluble vitamins, organic acids, fatty acids, amino acids, saccharides, pesticides, and endocrine disrupters.

For example, when the quantities of nutrients are to be clarified, examples of the test substance include thiamine (vitamin B1), riboflavin (vitamin B2), and N1-methylnicotinamide and N1-methyl-2-pyridone-5-carboxamide, which are each a metabolite of vitamin B3. Other examples thereof include water-soluble vitamins, such as N1-methyl-4-pyridone-3-carboxamide, pantothenic acid (vitamin B5), 4-pyridoxic acid (vitamin B6), biotin (vitamin B7), pteroylmonoglutamic acid (vitamin B9), and ascorbic acid (vitamin C). Other examples thereof include amino acids, such as L-tryptophane, lysine, methionine, phenylalanine, threonine, valine, leucine, isoleucine, and L-histidine. Other examples thereof include minerals, such as sodium, potassium, calcium, magnesium, and phosphorus, folic acid, cyanocobalamin and the like, and ascorbic acid.

(Quantitative Information)

The quantitative information is at least one selected from the group consisting of the quantity of the test substance contained in the sample, the concentration of the test substance contained in the sample, and presence or absence of the test substance in the sample. Moreover, the quantitative information is at least one selected from the group consisting of the ratio of the concentration or quantity of the test substance contained in the sample with respect to the reference quantity of the test substance, and the ratio between the quantities of the test substances contained in the sample or between the concentrations of the test substances.

(Calculation Method)

A calculation method according to this embodiment includes at least the following steps:
 (1) a reception step of receiving spectral information on a sample containing a test substance;
 (2) an acquisition step of acquiring a learning model relating to the spectral information on the test substance; and
 (3) a calculation step of calculating quantitative information on the test substance based on the spectral information on the sample and the learning model.

In those steps, the above-mentioned information is exemplified as the spectral information.

Moreover, the calculation method may include an analysis step of executing analysis for acquiring the spectral information on the sample, and the above-mentioned analysis is exemplified.

Moreover, the calculation method may further include a generation step of generating the learning models. The acquisition step may include a step of acquiring the learning models generated in the generation step. The learning model may be information containing the spectral information on the test substance and random noise. The random noise may be a waveform obtained through combination of a plurality of Gaussian functions.

The above-mentioned substances are exemplified as the test substances. The above-mentioned information is exemplified as the quantitative information.

The learning model may be generated through machine learning, for example, deep learning.

The calculation method may further include a display control step of controlling the display of the quantitative information.

An example of the calculation method according to the embodiment of the present invention is now described in detail.

(Data Analysis Method)

Figure 8:
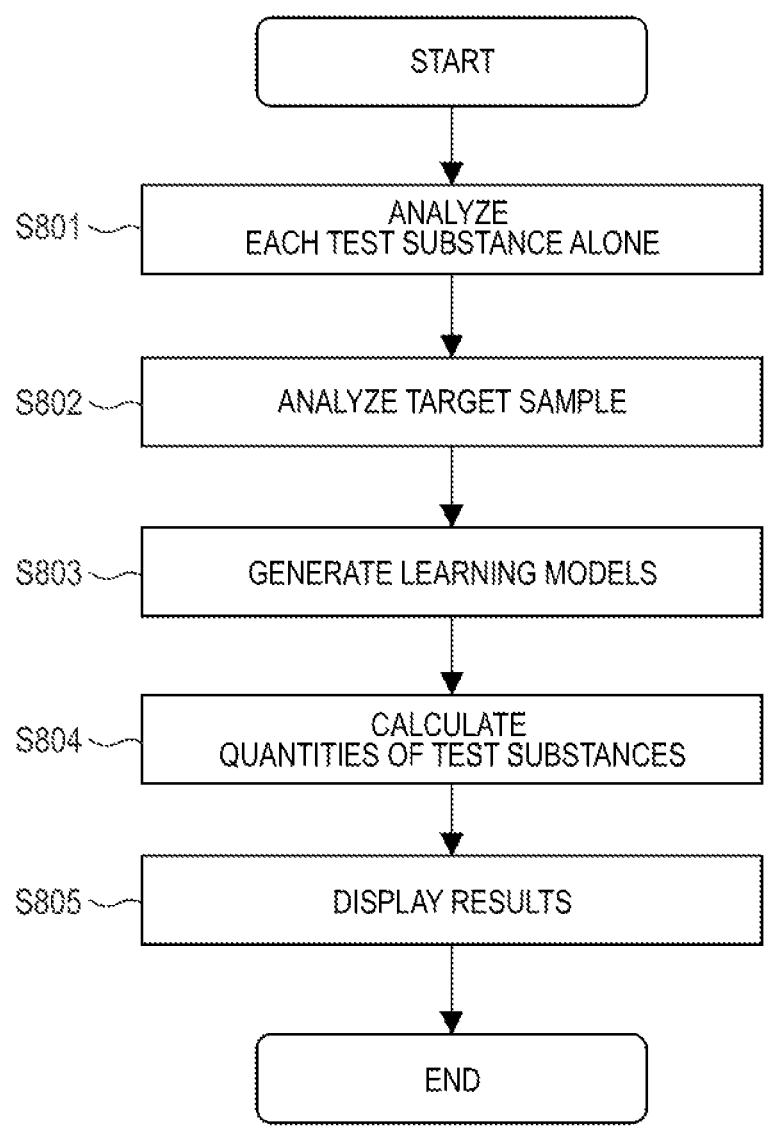
FIG. 8 is an example of a flowchart of processing for calculating the quantities of test substances in a sample in the second embodiment of the present invention.

With reference to FIG. 8, the processing in the calculation apparatus is now described in more detail. FIG. 8 is a flowchart of processing of calculating the quantity of each test substance in the sample.

(Step S801)

First, the analysis unit analyzes each test substance alone (Step S801). It is only required to appropriately select analysis conditions in terms of the sensitivity, the period of time required for the measurement, and the like. In the analysis, the measurement may be made at several different concentrations of each test substance. The required number of concentrations depends on a property of the substance and the like, and it is desired that the number be generally three or more. When a plurality of types of test substances exist, it is desired to measure each type. However, when signals of the test substances are sufficiently separated from one another, the measurement may be made simultaneously.

(Step S802)

Subsequently, the analysis unit analyzes the target sample containing the test substances (Step S802). Measurement conditions are set to the same conditions as those in Step S801.

(Step S803)

Subsequently, the generation unit uses the measurement results of each test substance alone acquired in Step S801 to generate a plurality of pieces of training data. The generation unit uses the generated training data to execute machine learning in accordance with a predetermined algorithm, to thereby build learning models (Step S803). As a specific method for the learning, for example, the neural network, the support vector machine, or the like may be used as a general machine learning method. Moreover, as a deep learning method having a plurality of hidden layers, the deep neural network (DNN), the convolutional neural network (CNN), or the like may be used. When a plurality of types of test substances exist, the learning model is built for each substance.

(Step S804)

Subsequently, the calculation unit applies the learning model generated in Step S803 to the measurement data acquired in Step S802, to thereby calculate the quantity of each test substance (Step S804). In this calculation, the quantity is converted to the form for the display on the display unit. The form displayed on the display unit may be a concentration such as g/L and mol/L or a ratio to a reference quantity (standard quantity).

(Step S805)

Subsequently, the display unit displays the quantities of the test substances calculated in Step S804, to thereby present the quantities to the user. In this display, the quantities may be arranged and displayed in a graph form or a table form.

The present invention can also be implemented by processing of supplying a program for implementing one or more functions of the above-mentioned embodiment to a system or an apparatus through a network or a recording medium and reading out and executing the program by one or more processors included in a computer of the system or the apparatus. Moreover, the present invention can also be implemented by a circuit (for example, an ASIC) configured to implement the one or more functions.

The present invention is now described in more detail by way of Examples and Comparative Examples, but the present invention is not limited to the following Examples.

EXAMPLES

Example 1

Figure 9:
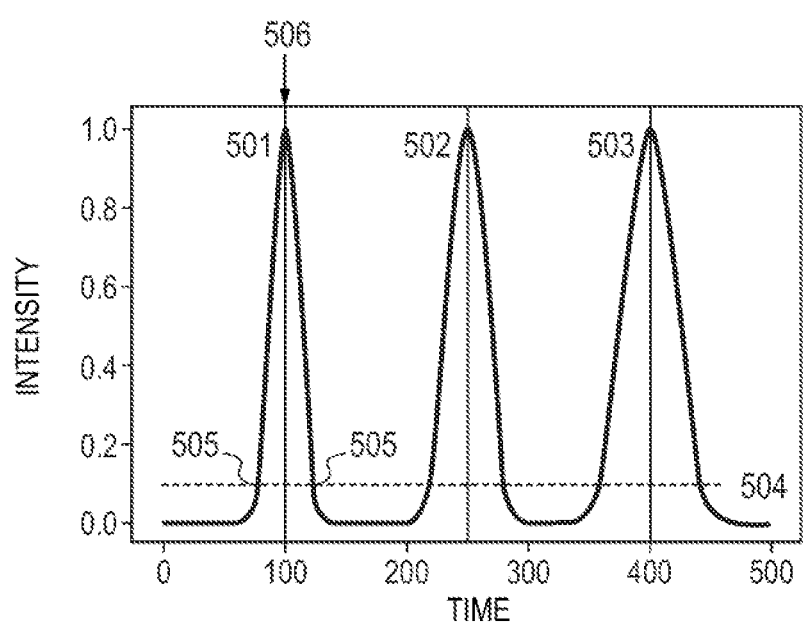
FIG. 9 is a graph for showing an example of a chromatogram including three types of test substances in Example 1 of the present invention.

FIG. 9 is a chromatogram including three types (501, 502, and 503) of test substances. As a threshold value 504, 0.1 was set. A peak position of each test substance was extracted from intersections between the threshold value and the chromatogram. For example, for the peak 501, a median value 506 of the intersections 505 each between the threshold value and the chromatogram was set as the position of the peak 501. Similarly, the peak positions of the peaks 502 and 503 were identified. The respective peak positions were 100, 250, and 400.

For each peak, a range of ±75 from the peak position was multiplied by values of from 0 to 1.8 (in increments of 0.2), to thereby obtain ten types of waveforms different in peak height. The waveforms different in peak height of the test substances 501, 502, and 503 were combined, to thereby generate 10×10×10=1,000 waveforms. The waveforms are hereinafter referred to as "test substance data." Five normal distribution waveforms each having the median value, the standard deviation, and the peak height set from random numbers were added to each piece of substance data, to thereby form sample data. The added normal distribution waveforms had a range of the peak height ("a" of Expression 1) of from 0.0 to 1.5, a range of the median value ("b" of Expression 1) of from 10 to 490, and a range of the standard deviation ("c" of Expression 1) of from 10 to 100, which were determined from the random numbers. For one piece of test substance data, 100 types of sample data were prepared. Each piece of sample data and the peak height of the test substance data contained in the sample data were combined, to thereby form 100,000 pieces of training data, and the training data was used for the machine learning to generate a learning model. As a method for the machine learning, a fully connected neural network was used. A ReLU function and a linear function were used as activation functions. A mean square error was used as a loss function. Adam was used as an optimization algorithm. In order to achieve a sufficient quantification accuracy, iterative calculation as many as about 20 epochs were required.

Figure 10:
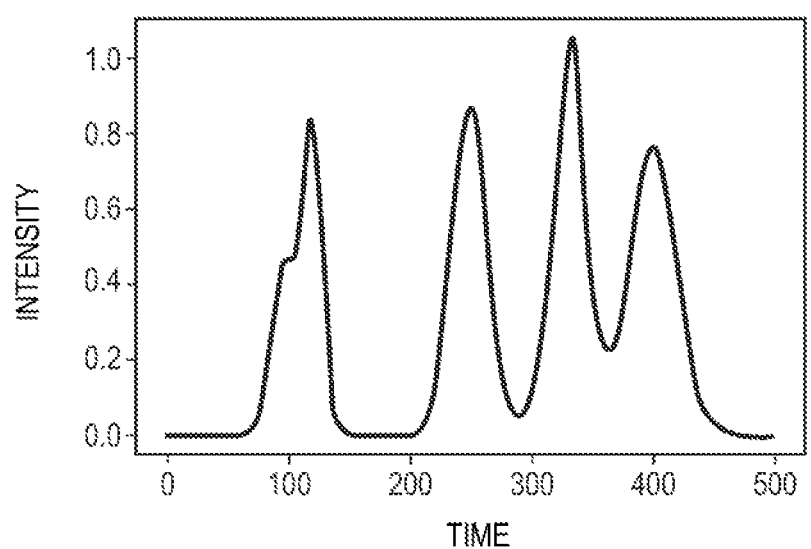
FIG. 10 is a graph for showing an example of a chromatogram including a plurality of different components in addition to the three types of test substances in Example 1 of the present invention.
Figure 11:
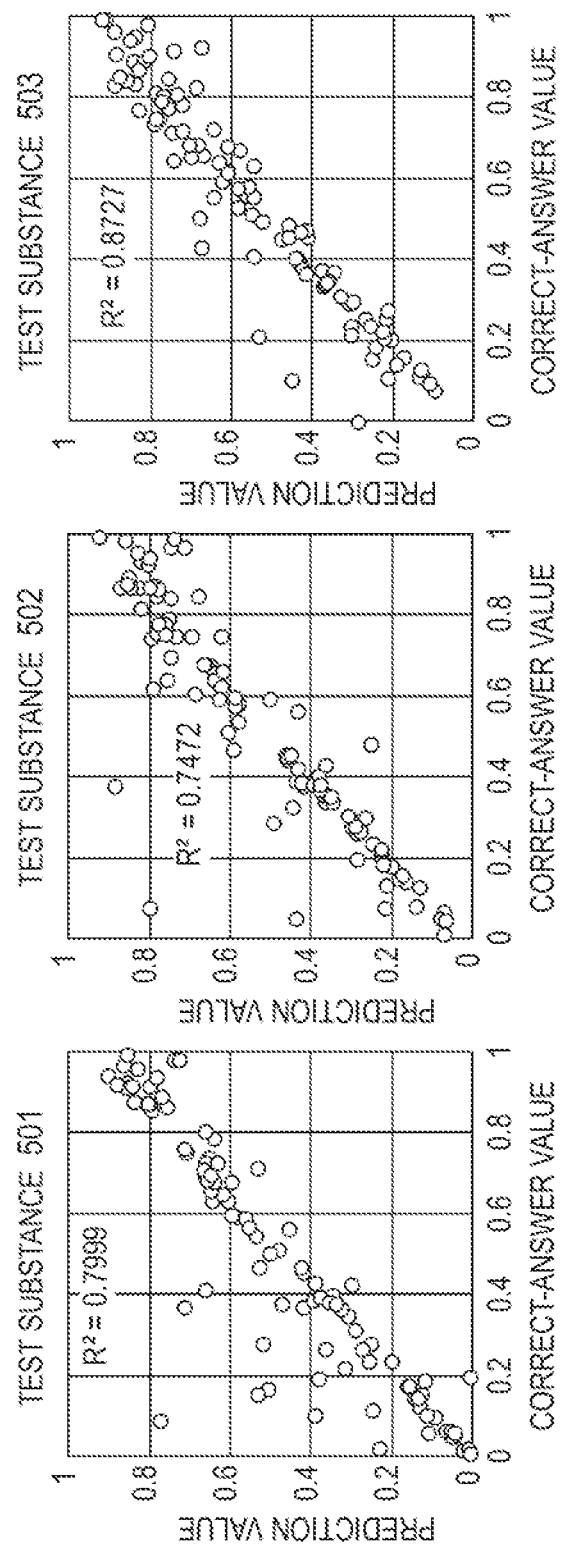
FIG. 11 shows graphs for showing prediction results of peak heights of the test substances through use of learning models in Example 1 of the present invention.

FIG. 10 is an example of a chromatogram of a plurality of components in addition to the three types of test substances of FIG. 9. The quantities of the three types of test substances were adjusted to any quantities. FIG. 11 is a graph at the time when the chromatogram formed of the plurality of components in addition to the three types of test substances as described above were applied to the learning model for showing a comparison between the calculated peak height (predicted value) of each of the test substances and the peak height (correct-answer value) of each of the test substances freely adjusted. It was able to make prediction at about 0.7 to 0.9 in terms of a correlation coefficient with respect to the correct-answer value.

Example 2

As in Example 1, the chromatogram of FIG. 9 was split into the ranges corresponding to the three types of test substances, and the ranges were multiplied by the values of from 0 to 1.8 (in increments of 0.2), to thereby obtain ten types of test substance data different in peak height for each test substance. Four normal distribution waveforms each having the median value, the standard deviation, and the peak height set from random numbers were added to each piece of substance data, to thereby form sample data. For one piece of test substance data, 1,000 types of sample data were prepared. Each piece of sample data and the peak height of the test substance data contained in the sample data were combined, to thereby form 10,000 pieces of training data, and the training data was used for the machine learning for each test substance to generate a learning model. As a method for the machine learning, a fully connected neural network was used. A ReLU function and a linear function were used as activation functions. A mean square error was used as a loss function. Adam was used as an optimization algorithm. In order to achieve a sufficient quantification accuracy, iterative calculation as many as about 100 epochs were required.

Figure 12:
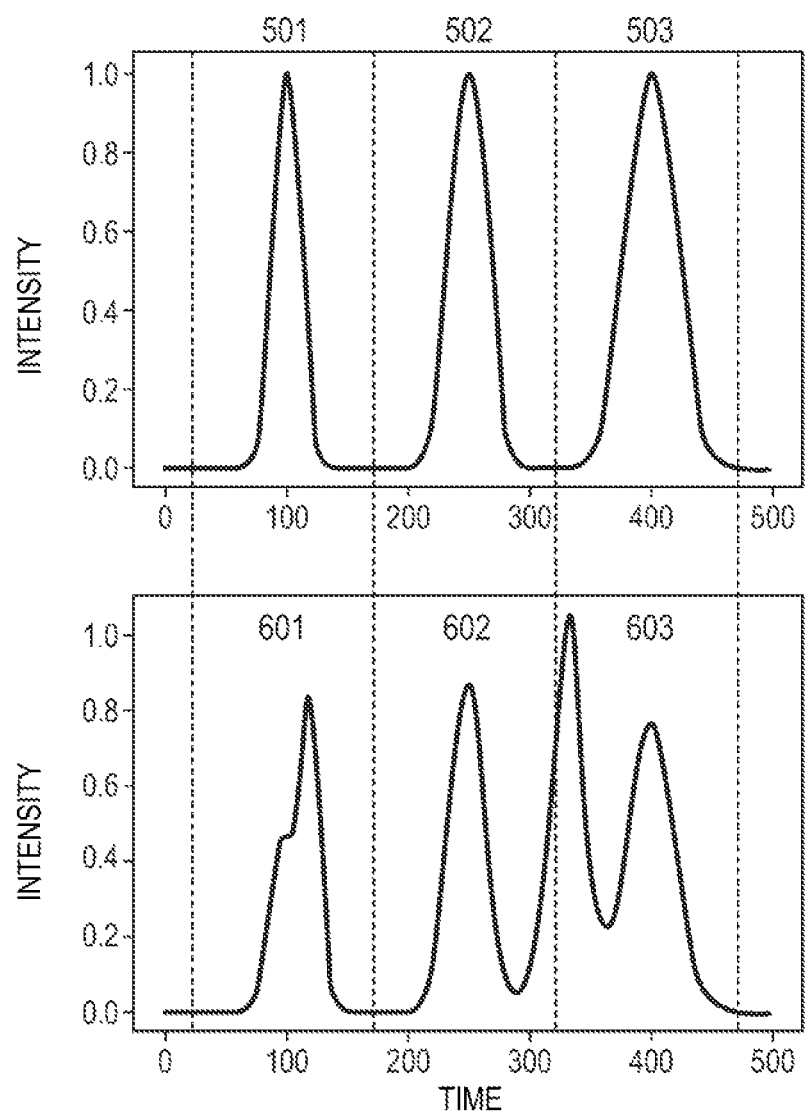
FIG. 12 shows graphs for showing a splitting method for spectral information in Example 2 of the present invention.
Figure 13:
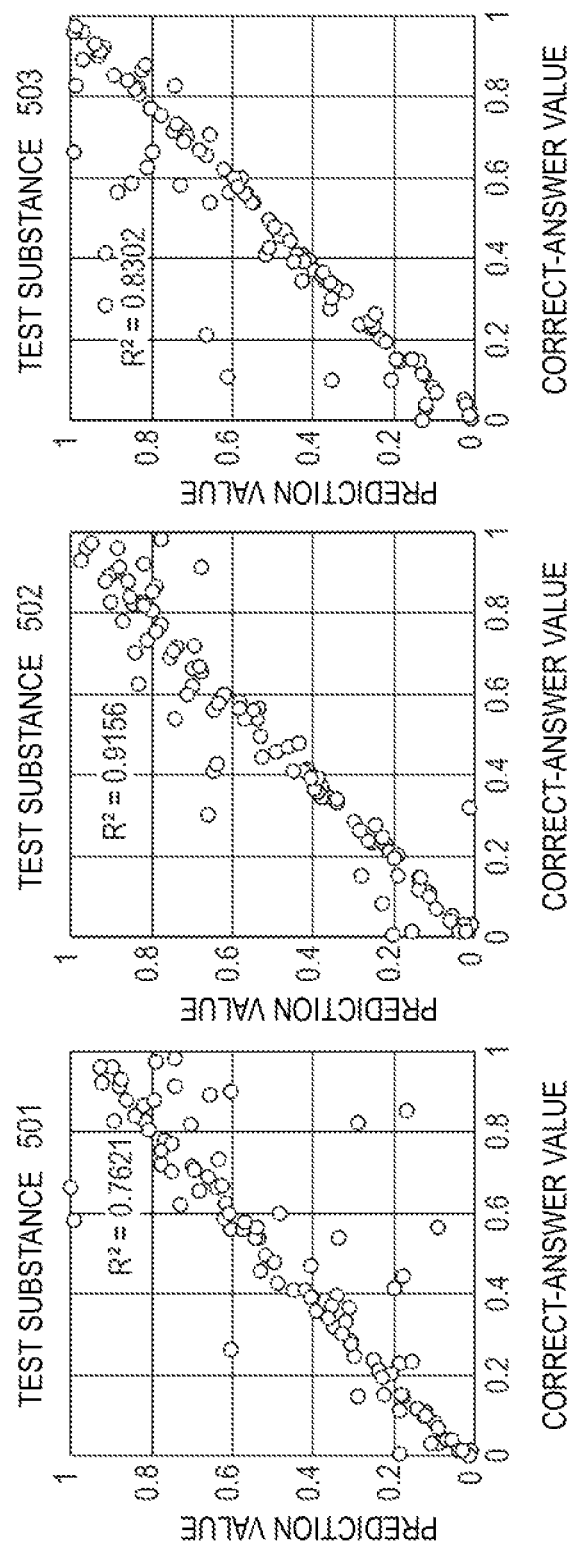
FIG. 13 shows graphs for showing prediction results of peak heights of test substances through use of learning models in Example 2 of the present invention.

A chromatogram of a plurality of different components in addition to the three types of test substances in any quantities was prepared as in Example 1. After that, the chromatogram was split into the same regions as those of the test substance data (501, 502, and 503) as shown in FIG. 12. After that, a chromatogram (601, 602, or 603) in the region corresponding to each test substance was applied to the learning model created for each test substance, to thereby calculate the peak of each test substance (predicted value). FIG. 13 is a graph of comparison while the peak height of the test substance adjusted freely was used as correct-answer values. It was able to make prediction at about 0.8 to 0.9 in terms of a correlation coefficient with respect to the correct-answer value.

Example 3

The standard deviation of each normal distribution waveform added to the test substance data in Example 2 was set as given below in accordance with tendency of the chromatogram.

Standard deviation=(random number 0-5)+time× 0.2+5

Figure 14:
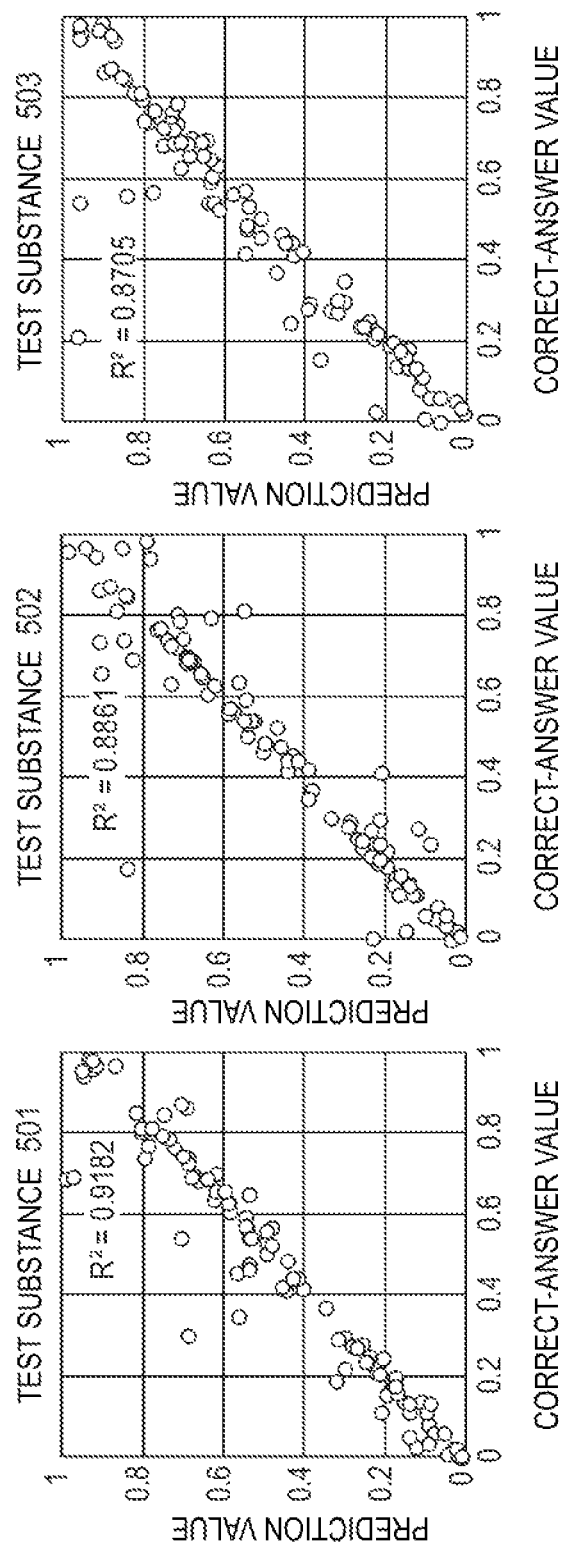
FIG. 14 shows graphs for showing prediction results of peak heights of test substances through use of learning models in Example 3 of the present invention.

The other settings were the same as those in Example 2, and the correct-answer value and the predicted value were compared with each other (FIG. 14). It was able to make prediction at about 0.9 as given by a correlation coefficient.

Example 4

Figure 15:
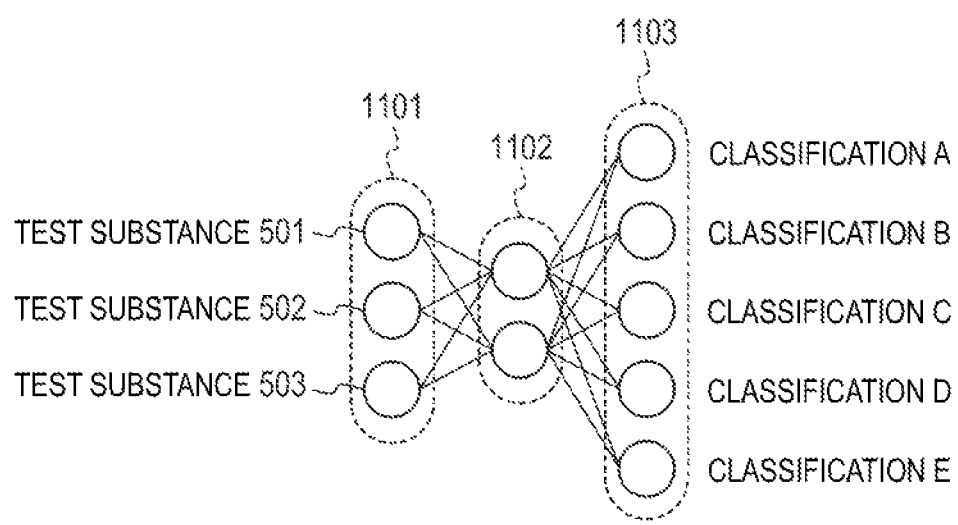
FIG. 15 is a diagram for illustrating an example of a learning model for predicting relating information from peak heights in Example 4 of the present invention.
Figure 16:
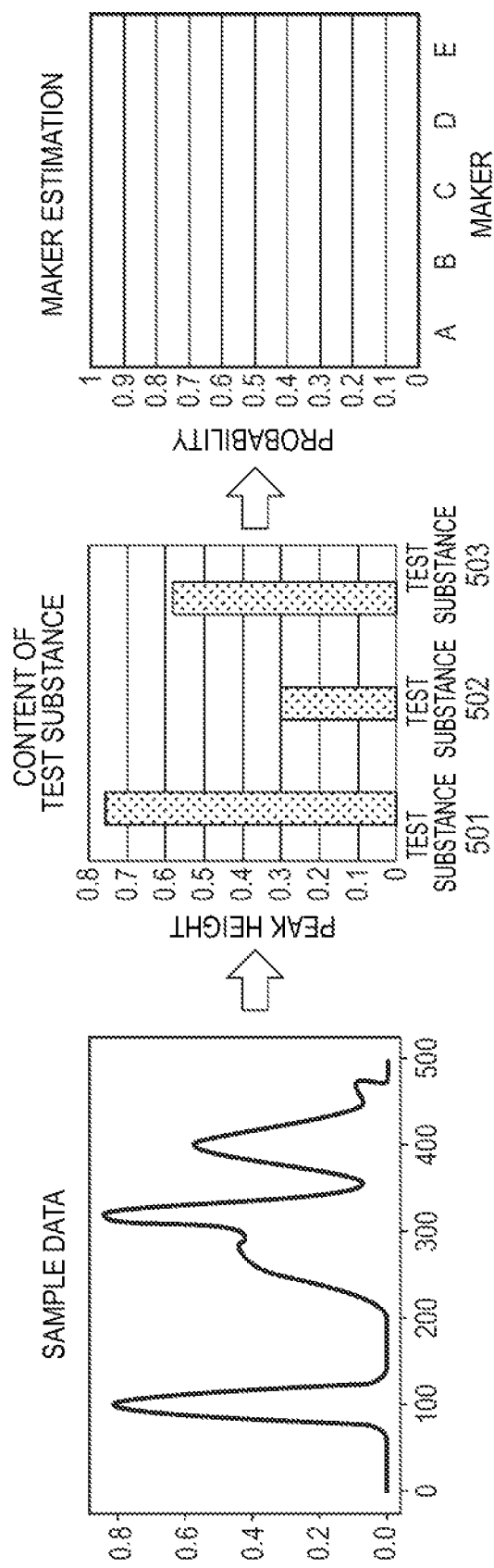
FIG. 16 shows graphs for showing prediction results of relating information from peak heights in Example 4 of the present invention.

The peak height was obtained as the final output in Example 1 to Example 3. In Example 4, means for predicting relating information from the peak height is implemented. It is known that a maker of the sample can be predicted in accordance with the ratios of the quantities of the test substances 501 to 503. There is prepared a learning model which has machine-learned, in advance, training data, each piece of which is formed of the quantities of the test substances 501 to 503 in the sample supplied by each of makers (five types of from A to E in this example) and the maker. FIG. 15 is a diagram for illustrating an example of a learning model using a fully connected neural network. Reference numeral 1101 denotes an input layer. The input layer 1101 inputs information corresponding to the quantities of the test substances 501 to 503. Reference numeral 1102 denotes an intermediate layer. In this example, there is one intermediate layer, but there may be prepared a plurality of layers in accordance with the numbers of test substances and classifications. Moreover, the number of nodes may also appropriately be changed. Reference numeral 1103 denotes an output layer. The classifications A to E correspond to the respective makers. Activation functions that connect the intermediate layer and the output layer to each other are softmax functions. An output of the softmax function is a probability. The quantity (calculated from the peak height) of each test substance acquired in Example 1 to Example 3 was applied to the learning model in this embodiment, to thereby display a probability that each maker has manufactured the sample containing the test substances. An example of the results is shown in FIG. 16.

Example 5

First, there is now described an example in which the method was applied to simulation data in order to evaluate an effect of the above-mentioned method for the data processing.

As the test substance data, 11 types of data represented by normal distribution waveforms having a median value of 250, a standard deviation of 20, and a peak height of from 0.0 to 1.0 in increments of 0.1 were prepared. The range of the data (trimming range) was set to 0 to 500.

Four normal distribution waveforms each having the median value, the standard deviation, and the peak height set from random numbers were added to each piece of substance data, to thereby form sample data. The added normal distribution waveforms had a range of the peak height ("a" of Expression 1) of from 0.0 to 1.5, a range of the median value ("b" of Expression 1) of from 10 to 490 (±240 from the peak center value of the test substance), and a range of the standard distribution ("c" of Expression 1) of from 10 to 100, which were determined from the random numbers. For one piece of test substance data, 1,000 types of sample data were prepared. Each piece of sample data and the peak height of the test substance data contained in the sample data were combined, to thereby form 11,000 pieces of training data, and the training data was used for the machine learning to generate a learning model. As a method for the machine learning, a fully connected neural network was used. A ReLU function and a linear function were used as activation functions. A mean square error was used as a loss function. Adam was used as an optimization algorithm. In order to achieve a sufficient quantification accuracy, iterative calculation as many as about 100 epochs were required.

Figure 17:
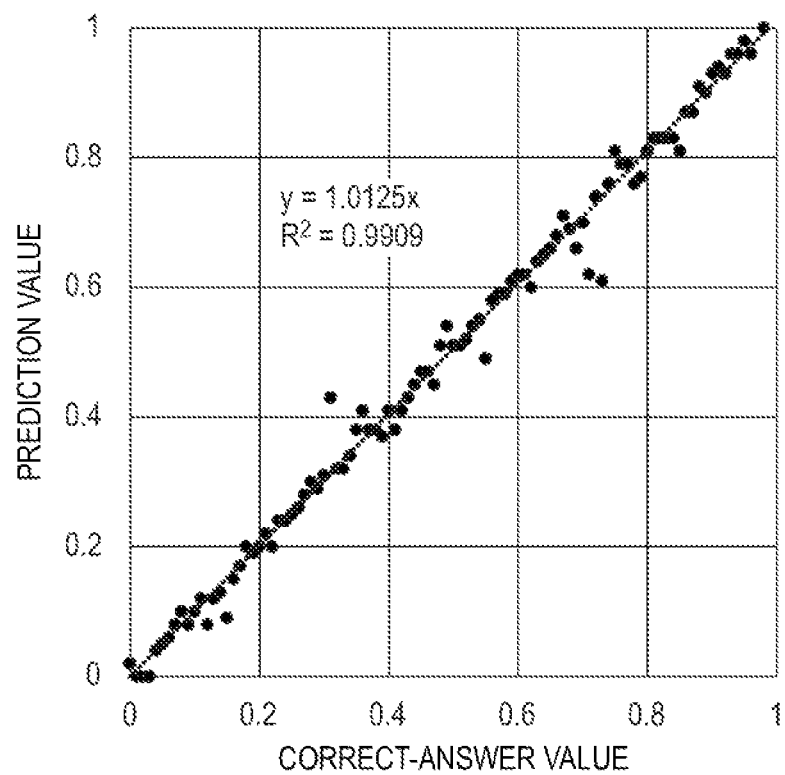
FIG. 17 is a graph for showing prediction results of the peak height of a test substance through use of a learning model in Example 5 of the present invention.

Data created by the same method as that for the sample data was applied to the acquired learning models, to thereby obtain the peak heights of the test substances contained in the sample data. The horizontal axis of FIG. 17 represents the peak heights (correct-answer values) of the test substances used to create the sample data. The vertical axis represents the peak heights (predicted values) of the test substances obtained through the learning models. The correlation coefficient between the correct-answer values and the predicted values was 0.99.

Figure 5:
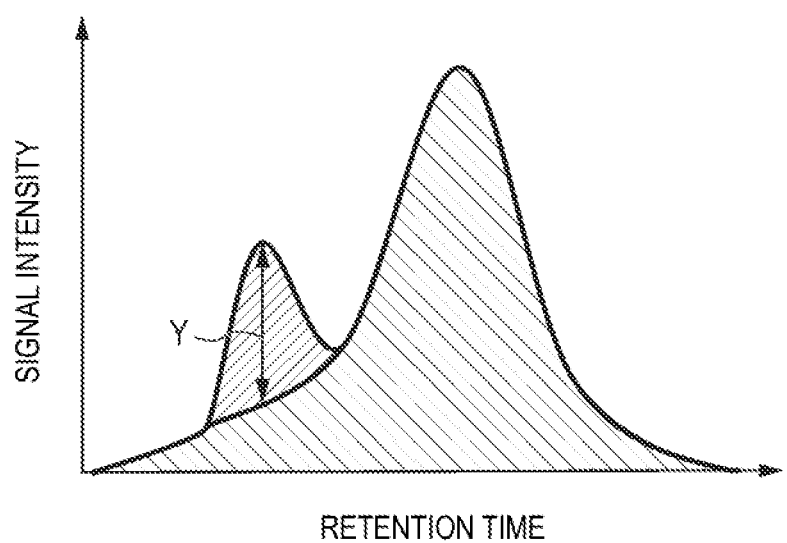
FIG. 5 is a graph for showing an example of a related-art peak splitting method of providing a baseline.
Figure 6:
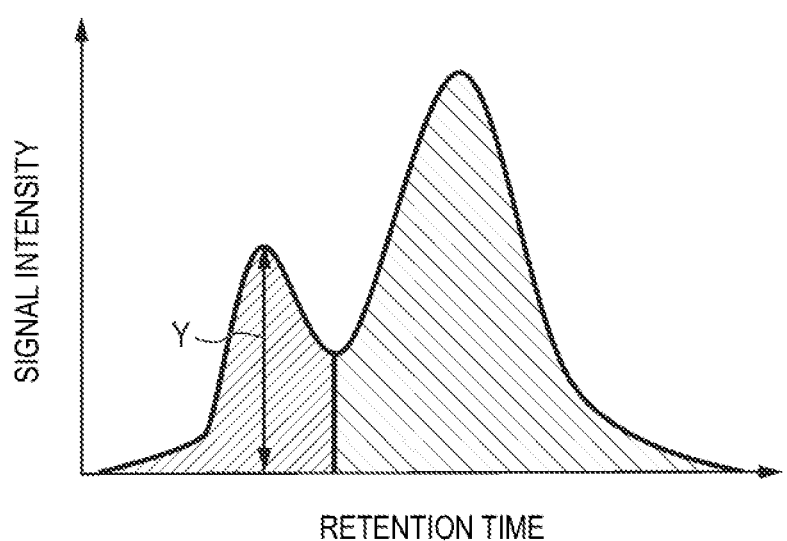
FIG. 6 is a graph for showing an example of a related-art peak splitting method of vertically splitting a spectrum through use of a minimal value between peaks.
Figure 18:
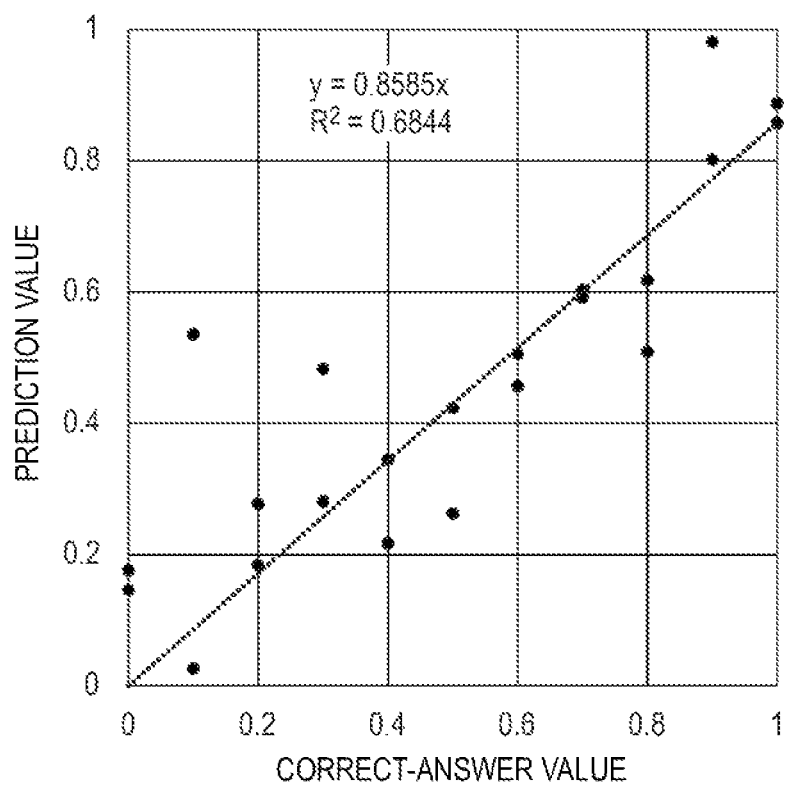
FIG. 18 is a graph for showing prediction results of the peak height of the test substance through use of the related-art method (FIG. 5).

Moreover, in FIG. 18, there is shown, as a comparative example, a case in which the related-art peak splitting method (method of providing the baseline (FIG. 5)) was applied to data created by the same method as that for the sample data. The correlation coefficient between the correct-answer values and the predicted values was 0.68.

Example 6

In order to evaluate the effects of the above-mentioned data processing method, an example in which the method is applied to the quantitative determination of urinary 1,6-dihydro-1-methyl-6-oxo-3-pyridinecarbamide (hereinafter referred to as 2py), which is one of the metabolites of vitamin B3, is described. Actually measured waveforms were prepared by measuring 2py (0.0 µg/mL, 2.5 µg/mL, 5.0 µg/mL, 7.5 µg/mL, and 10 g/mL) by HPLC. Trimming was performed within the range of retention time of from 100 to 400, four normal distribution waveforms in which a median value, standard deviation, and a peak height were set by random numbers were added to the actually measured waveform of 2py by HPLC. Thus, sample data was created. Based on the facts that the peak median value, the standard deviation, and the assumed maximum peak height of 2py were 250, about 10, and 500, respectively, the peak height ("a" of Expression 1), the median value ("b" of Expression 1), and the standard deviation ("c" of Expression 1) were determined by random numbers in the ranges of from 0 to 750, from 130 to 370, and from 5 to 50, respectively. 1,000 sample data were prepared for one data on 2py. Machine learning was performed by using 5,000 training data obtained by combining each sample data and the data on the peak height of 2py contained therein. Thus, a learning model was generated. The machine learning was performed in the same manner as in Example 5.

Figure 19:
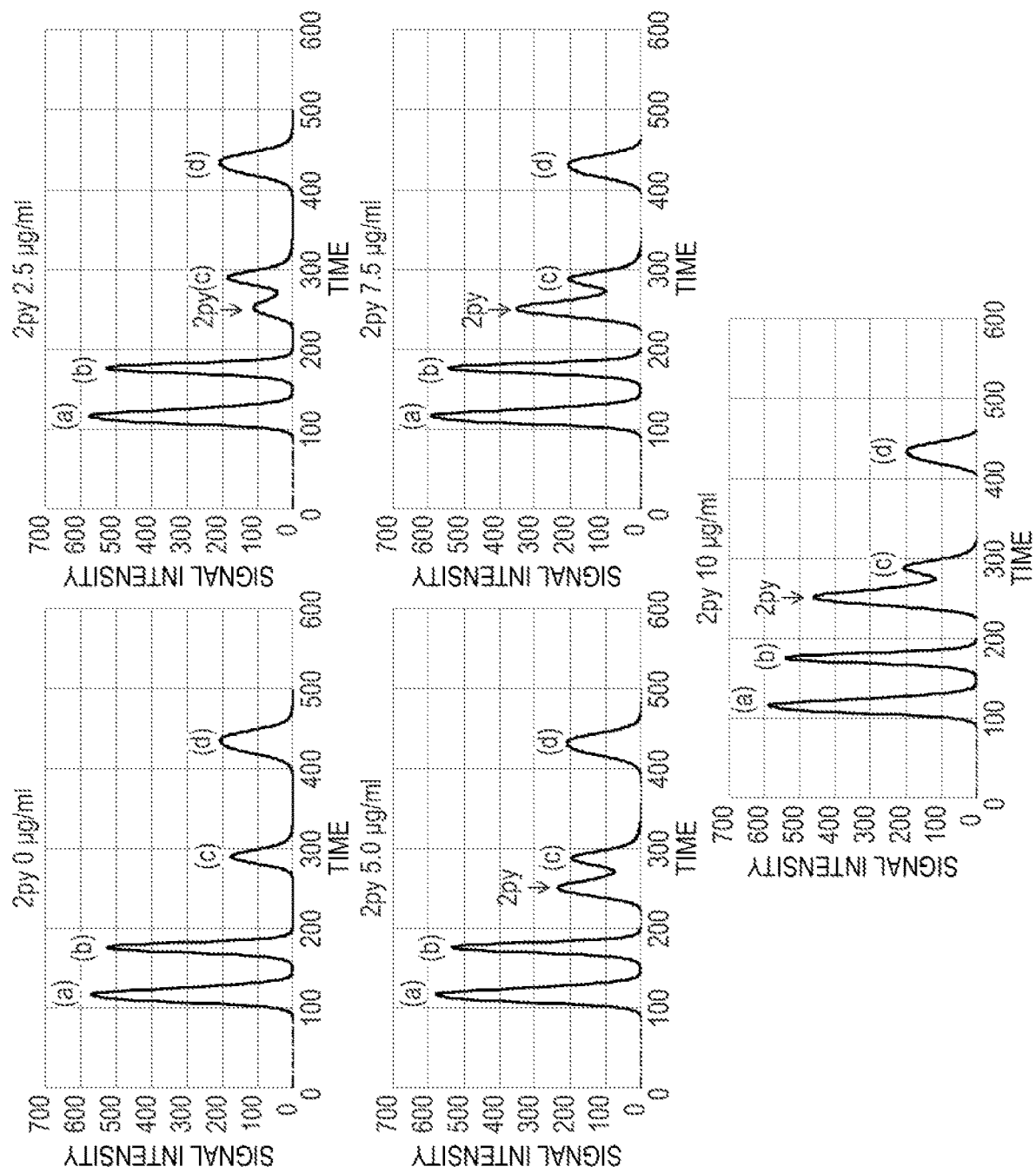
FIG. 19 shows graphs for showing chromatograms acquired through HPLC analysis in Example 6 of the present invention.
Figure 20:
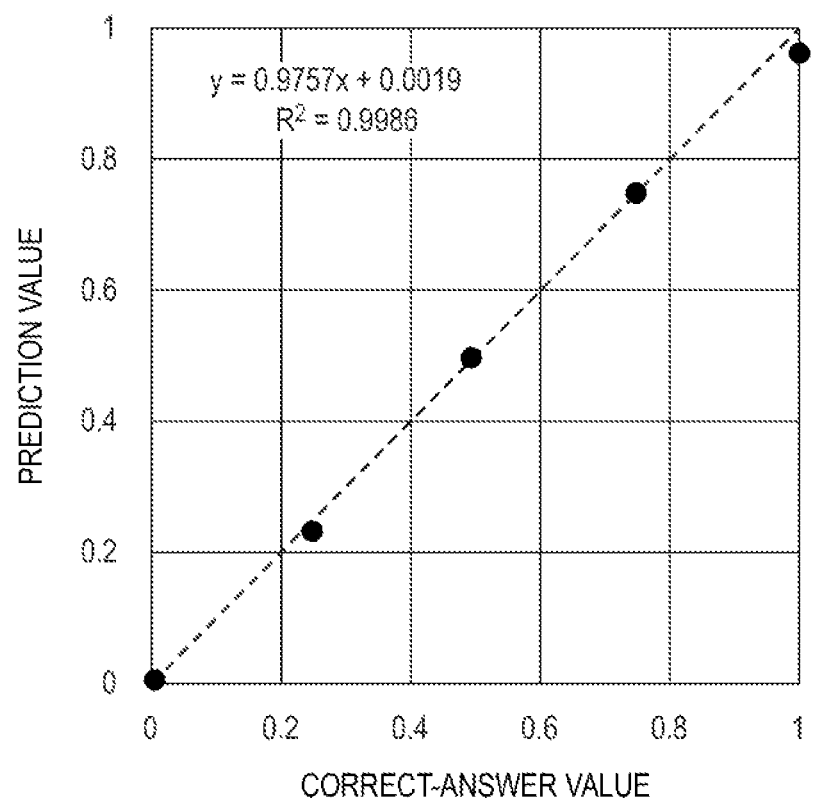
FIG. 20 is a graph for showing prediction results of the peak height of a test substance through use of a learning model in Example 6 of the present invention.

Next, samples containing 2py (0.0 µg/mL, 2.5 µg/mL, 5.0 µg/mL, 7.5 µg/mL, and 10 µg/mL) and other impurities were analyzed by HPLC to obtain chromatograms of FIG. 19. The other impurities include (a: uric acid, b: trans-urocanic acid, c: N1-methyl-4-pyridone-3-carboxamide, and d: adenosine). Each chromatogram was applied to the learning model having been generated, and the peak height corresponding to 2py was predicted. As a result, the correlation coefficient between the correct-answer values and the predicted values was 0.99 (FIG. 20). The peak of 2py was in contact with the peak of the impurity (c), but the peak height was able to be predicted without any problem.

Example 7

Figure 21:
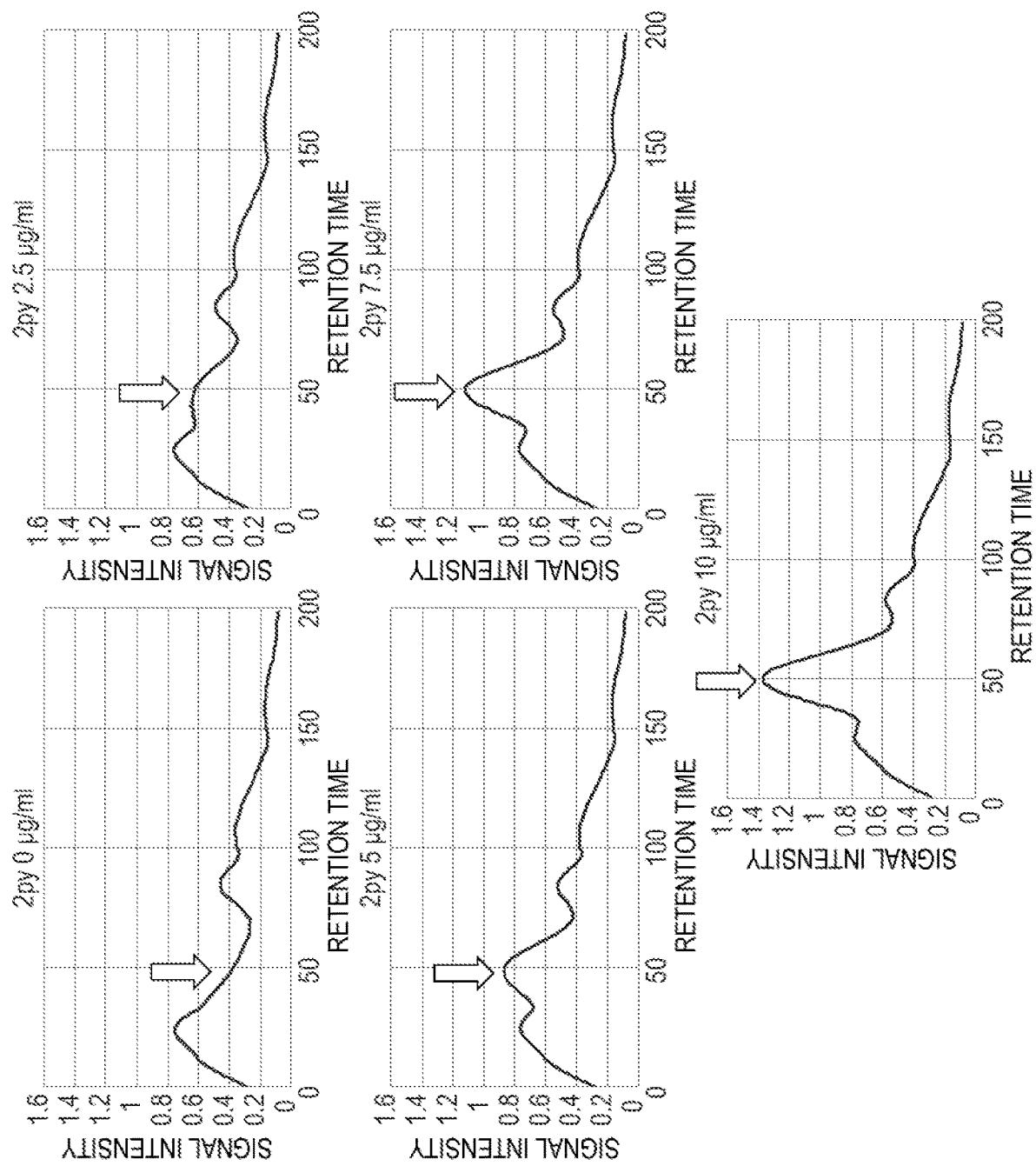
FIG. 21 shows graphs for showing chromatograms acquired in Example 7 of the present invention.
Figure 22:
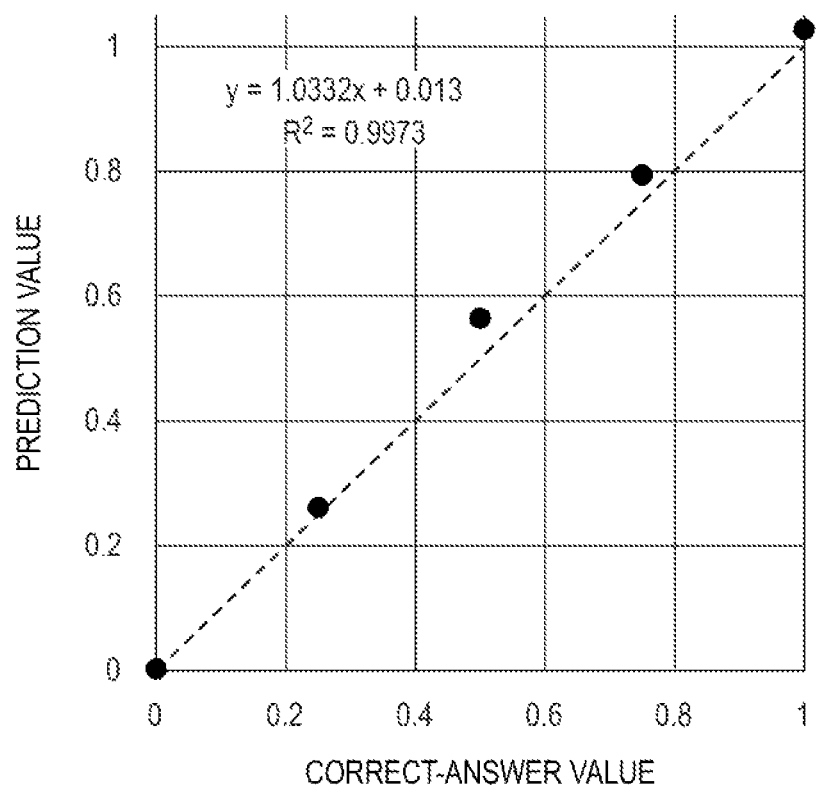
FIG. 22 is a graph for showing the prediction results of the peak height of a test substance through use of a learning model in Example 7 of the present invention.

As Example in which impurities are contained in larger quantities, an example in which the method is applied to the quantitative determination of 2py having been added to "No Additive Vegetables 48 Kinds of Dense Vegetables 100% (hereinafter referred to as "vegetable juice")" manufactured by Kirin Holdings Company, Limited is described. The waveforms of 2py were measured by HPLC in advance in the same manner as in Example 6, and thus a learning model was generated. Trimming was performed within the range of retention time of from 0 to 200. The peak height ("a" of Expression 1), the median value ("b" of Expression 1), and the standard deviation ("c" of Expression 1) were determined by random numbers in the ranges of from 0.0 to 1.5, from 0 to 290, and from 10 to 100, respectively. Four normal distribution waveforms were added to the waveform of 2py. Thus, sample data was created. The vegetable juice was allowed to pass through a filter of 0.8 µm in advance to remove coarse particles therefrom, and was subjected to pretreatment with MonoSpin C18 manufactured by GL Sciences Inc. The pretreatment was performed through centrifugal separation at 10,000 rpm. 2py (0.0 g/mL, 2.5 µg/mL, 5.0 µg/mL, 7.5 µg/mL, and 10 µg/mL) was added to the vegetable juice after the pretreatment, and the resultant was analyzed by HPLC to obtain chromatograms of FIG. 21. In each figure, a portion represented by the arrow corresponds to the retention time of 2py. In the same manner as in Example 6, each chromatogram was applied to the learning model having been generated, and the peak height corresponding to 2py was predicted. As a result, the correlation coefficient between the correct-answer values and the predicted values was 0.99 (FIG. 22). It was revealed that, even in a system in which impurities were contained in large quantities and a zero baseline was not obtained, the peak height of 2py serving as a test substance was able to be predicted without any problem.

According to the information processing apparatus and the calculation apparatus of the present invention, it is possible to acquire highly accurate information on the test substances from the spectral information without the preprocessing for separating the impurities and the calculation processing, for example, the peak splitting method.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An information processing apparatus comprising:
a processor; and
a memory containing instructions that, when executed by the processor, cause the processor to function as:
an estimation means for estimating quantitative information on a test substance by inputting spectral information on a sample containing the test substance and impurities into a learning model; and
an information acquisition means for acquiring the quantitative information estimated by the estimation means,
wherein the learning model is learned through use of training data, the training data being a plurality of combinations of data each formed of (a) quantitative information on a test substance as correct-answer data, and (b) spectral information on the test substance at the respective quantity and random noise added thereto as input data on a virtual sample containing the test substance and impurities.

2. The information processing apparatus according to claim 1, wherein the sample contains a plurality of types of test substances.

3. The information processing apparatus according to claim 2, wherein the information acquisition means further includes a splitting unit configured to split the spectral information on the sample into spectral information on each test substance.

4. The information processing apparatus according to claim 3, wherein the splitting unit is configured to split the spectral information at a splitting location of the spectral information, the splitting location being specified by a user.

5. The information processing apparatus according to claim 3, wherein the splitting unit is configured to split the spectral information by extracting a position of the spectral information and a certain range containing the position, the position being specified by a user.

6. The information processing apparatus according to claim 3, wherein the splitting unit is configured to split the spectral information by extracting a range of the spectral information in which a threshold value set in advance is exceeded.

7. The information processing apparatus according to claim 1, further comprising display control means for causing a display unit to display the acquired quantitative information.

8. The information processing apparatus according to claim 7,
wherein the sample contains a plurality of types of the test substances, and
wherein the display control means is configured to select and display information specified by a user from the quantitative information on the plurality of types of test substances.

9. The information processing apparatus according to claim 1, wherein the random noise is obtained by combining a plurality of Gaussian functions.

10. The information processing apparatus according to claim 1, wherein the random noise is generated through use of a random number and partial spectral information selected from the spectral information on the test substance, and the random noise is determined based on the partial spectral information.

11. The information processing apparatus according to claim 1, wherein the spectral information is at least one kind selected from the group consisting of a chromatogram, a photoelectron spectrum, an infrared absorption spectrum, a nuclear magnetic resonance spectrum, a fluorescence spectrum, a fluorescent X-ray spectrum, an ultraviolet/visible absorption spectrum, a Raman spectrum, an atomic absorption spectrum, a flame emission spectrum, an optical emission spectrum, an X-ray absorption spectrum, an X-ray diffraction spectrum, a paramagnetic resonance absorption spectrum, an electron spin resonance spectrum, a mass spectrum, and a thermal analysis spectrum.

12. The information processing apparatus according to claim 1, further comprising analysis means for executing analysis for acquiring the spectral information on the sample.

13. The information processing apparatus according to claim 12, wherein the analysis means is configured to use at least one kind of method selected from the group consisting of chromatography, capillary electrophoresis, photoelectron spectroscopy, infrared absorption spectroscopy, nuclear magnetic resonance spectroscopy, fluorescence spectroscopy, fluorescence X-ray spectroscopy, visible/ultraviolet absorption spectroscopy, Raman spectroscopy, atomic absorption spectroscopy, flame emission spectroscopy, optical emission spectroscopy, X-ray absorption spectroscopy, X-ray diffractometry, electron spin resonance spectroscopy, mass spectroscopy, and thermal analysis.

14. The information processing apparatus according to claim 1, wherein the test substance is at least one kind selected from the group consisting of thiamine, riboflavin, N1-methylnicotinamide, N1-methyl-2-pyridone-5-carboxamide, N1-methyl-4-pyridone-3-carboxamide, pantothenic acid, pyridoxine, 4-pyridoxic acid, biotin, cyanocobalamin, and ascorbic acid.

15. The information processing apparatus according to claim 1, wherein the quantitative information is at least one kind selected from the group consisting of a quantity of the test substance contained in the sample, a concentration of the test substance contained in the sample, presence or absence of the test substance in the sample, a ratio of the concentration or the quantity of the test substance contained in the sample with respect to a reference quantity of the test substance, and a ratio between quantities of the test substances contained in the sample or between concentrations of the test substances.

16. The information processing apparatus according to claim 1, wherein the random noise is a waveform obtained by adding a plurality of Gaussian functions each having a peak height, a median value, and a standard deviation determined from random numbers to one another.

17. A control method for an information processing apparatus that includes processor and a memory containing instructions that, when executed by the processor, cause the processor to execute the control method comprising:
an estimation step of estimating quantitative information on a test substance by inputting spectral information on a sample containing the test substance and impurities into a learning model, and an information acquisition step of acquiring the quantitative information estimated in the estimation step,
wherein the learning model is learned through use of training data, the training data being a plurality of combinations of data each formed of (a) quantitative information on a test substance as correct-answer data, and (b) spectral information on the test substance at the respective quantity and random noise added thereto as input data on a virtual sample containing the test substance and impurities.

* * * * *